US006380392B1

(12) United States Patent
Zhang

(10) Patent No.: US 6,380,392 B1
(45) Date of Patent: Apr. 30, 2002

(54) LIGANDS BASED ON CHIRAL 2-AMINO-2'-HYDROXY-1,1'-BINAPHTHYL AND RELATED FRAMEWORKS FOR ASYMMETRIC CATALYSIS

(75) Inventor: Xumu Zhang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/607,005

(22) Filed: Jun. 29, 2000

Related U.S. Application Data

(60) Provisional application No. 60/141,795, filed on Jun. 30, 1999.

(51) Int. Cl.[7] .................. C07D 213/53; C07D 333/22; C07F 7/28
(52) U.S. Cl. .................. 546/334; 549/75; 549/491; 556/33; 556/54; 556/134; 564/48; 564/305; 502/171
(58) Field of Search .................. 556/33, 54, 134; 544/224; 546/334; 549/75, 491; 564/48, 305; 502/171

(56) References Cited

U.S. PATENT DOCUMENTS 5,599,963 A * 2/1997 Carreira et al. .............. 556/33

OTHER PUBLICATIONS

"Binap: An Efficient Chiral Element for Asymmetric Catalysis" by Ryoji Noyori et al., 1990 Acc. Chem. Res., vol. 23, No. 10, pp. 345–350.

"Novel Two–Phase Oxidative Cross–Coupling of the Two Component Molecular Crystal of 2–Naphtol and 2–naphthylamine" by Kuiling Ding et al., Chem. Commun, 1997, pp. 693–694.

"A Facile Synthesis of 2–Amino–2'–hydroxy–1,1–binaphthyl and 2,2'–Diamino–1,1'–binaphthyl by Oxidative Coupling Using Copper (II) Chloride" by Martin Smrcina et al., Apr. 1991, Synlett, pp. 231–232.

"Synthesis and Resolution of Racemic 2–Amino–2'–Hydroxy–1,1'–Binaphthyl" by Martin Smrcina et al, Collect. Czech. Chem. Commun. (vol. 61), 1996, pp. 1520–1524.

"Derivatives of 2–Amino–2'Diphenylphosphino–1,1'–binaphthyl (MAP) and Their Application in Asymmetric Palladium(0)–Catalyzed Allylic Substitution" by Stephan Vyskocil et al., 1998 J. Org. Chem. vol. 63, No. 22, pp. 7738–7748.

"Synthesis of N–alkylated and N–Arylated Derivatives of 2–Amino–2'–hydroxy–1,1'–binaphthyl (NOBIN) and 2,2'–Diamino–1,1'–binaphthyl and Their Application in the Enantioselective Addition of Diethylzine to Aromatic Aldehydes" by Stephan Vyskocil et al., 1998 J. Org. Chem.., vol. 63, No. 22, pp. 7727–7727.

"Catalytic Enantioselective Acetone Aldol Additions With 2–Methoxypropene", by Erick M. Carreira et al., 1995, Am. Chem. Soc., vol. 117, No. 12, pp. 3649–3650.

"Catalytic Enantioselective Aldol Additions with Methyl and Ethyl Acetate O–Silyl Enolates: A Chiral Tridentate Chelate as a Ligand for Titanium (IV)", by Erick M. Carreira et al. 1994 J. Am. Chem. Soc, 116, pp. 8837–8838.

"Catalytic Enantioselective Dienolate Additions to Aldehydes: Preparation of Optically Active Acetoacetat Aldol Adducts", by Robert A. Singer et al., J. Am. Chem. Soc. 1995, vol. 117, No. 49, pp. 12360–12361.

"Copper–Catalyzed Enantioselective Michael Additions: Recent Progress With New Phosphorus Ligands" by Norbert Krause, Angew. Chem. Int. Ed., 1998, vol. 37, No. 3, pp. 283–285.

"Highly Enantioselective Catalytic Conjugate Addition and Tandem Conjugate Addition—Aldol Reactions of Organozinc Reagents" by Ben L. Feringa et al., Angew Chem. Int. Ed. Engl. 1997, vol. 36, No. 23, pp. 2620–2623.

"Novel Two–Phase Oxidative Cross–Coupling of the Two–Component Molecular Crystal of 2–Naphthol and 2–Naphthylamine" by Kuiling Ding et al., Chem. Commun., 1997, pp. 693–694.

"Catalytic Asymmetric Synthesis of Optically Active 2–Alkanols via Hydrosilyation of 1–Alkenes With A Chiral Monophosphine–Palladium Catalyst", by Yasuhiro Uozumi et al., 1991, J. Chem. Sco., vol. 113, pp. 9887–9888.

* cited by examiner

*Primary Examiner*—Charanjit S. Aulakh
(74) *Attorney, Agent, or Firm*—Ohlandt, Greeley, Ruggiero & Perle, L.L.P.

(57) ABSTRACT

The present invention includes array of new chiral ligands that are optically active or racemic. These ligands are bidentate, tridentate, tetradentate or pentadentate ligands which include P-P, P-N, N-N, mixed P-N, Schiff base or carbene sites. The present invention further includes a catalyst prepared by a process, which includes contacting a transition metal salt, or a complex thereof, and a ligand according to the present invention. The present invention still further includes a process for preparation of an asymmetric compound. In this process, a substrate capable of forming an asymmetric product by an asymmetric reaction and a catalyst according to the present invention are contacted to produce an asymmetric product. Transition metal complexes with these ligands are effective catalysts for asymmetric reactions. Applicant has discovered that asymmetric products can be prepared using the chiral catalysts according to the present invention in enantioselective reactions, such as hydrogenation, hydroformylation, Michael addition, Heck reaction, Aldol reaction, allylic alkylation, cyclopropanation, epoxidation, and olefin metathesis.

21 Claims, No Drawings

LIGANDS BASED ON CHIRAL 2-AMINO-2'-HYDROXY-1,1'-BINAPHTHYL AND RELATED FRAMEWORKS FOR ASYMMETRIC CATALYSIS

This application claims priority from Provisional Application Ser. No. 60/141,795 filed on Jun. 30, 1999.

BACKGROUND OF THE INVENTION

1. Field of the Invention

The present invention relates to ligands, transition metal complexes thereof and enantioselective processes based on the reactions of these complexes for forming a product with an enantiomeric excess of an optical isomer. More specifically, the present invention relates to chiral 2,2'-substituted-1,1'-binaphthyl ligands, Pd, Rh, Ru, Ir, Cu, Ni, Mo, Ti, V, Re and Mn complexes thereof and enantioselective processes based on hydrogenation, hydroformylation, allylic alkylation, cyclopropanation, Heck, Aldol, Michael addition and epoxidation reactions of these complexes to form an enantiomerically enriched product.

2. Description of the Prior Art

Design and synthesis of new chiral ligands play a crucial role in the development of transition metal-catalyzed asymmetric reactions. The symmetric (e.g., BINAP, Noyori, R.; Takaya, H. *Acc. Chem. Res.* 1990, 23, 345) and unsymmetrical (e.g., MOP, Uozumi, Y.; Hayashi, T. *J. Am. Chem. Soc.* 1991, 113, 9887) binaphthyl scaffolds have been demonstrated as effective ligands for a variety of asymmetric reactions.

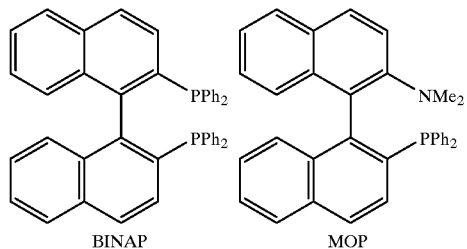

Chiral 2-amino-2'-hydroxy-1,1'-binaphthyl (NOBIN) developed by Kocovsky et al. has proven to be an excellent framework for constructing chiral ligands to conduct asymmetric catalytic reactions (see M. Smrcina et al., *Synlett.*, 1991, 231; S. Vyskocil et al., *J. Org. Chem.*, 1998, 63, 7727; and S. Vyskocil, *J. Org. Chem.*, 1998, 63, 7738).

Various synthetic routes and resolution methods for synthesizing NOBIN in large quantities have been tried (see M. Smrcina et al., *Collect. Czech. Chem. Commun.*, 1996, 61, 1520 and K. Ding et al., *J. Chem. Soc., Chem. Commun.*, 1997, 693). One of the most notable applications has been the use of NOBIN as the chiral backbone in Carreira's chiral aldol catalyst (see E. M. Carreira et al., *J. Am. Chem. Soc.*, 1994, 116, 8837; E. M. Carreira et al., *J. Am. Chem. Soc.*, 1995, 117, 3649 and R. A. Singer et al., *J. Am. Chem. Soc.*, 1995, 117, 12360).

Several chiral ligands that are described in the prior art are summarized below.

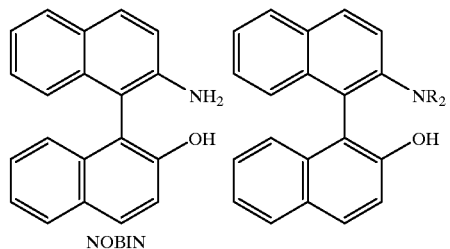

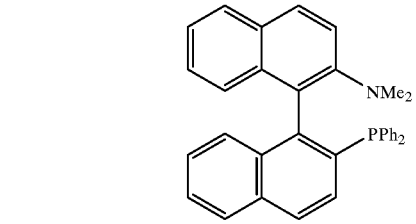

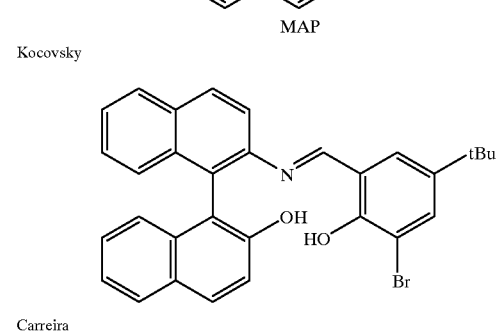

Chiral ligands made from 2-amino-2'-hydroxy-1,1'-binaphthyl framework

None of the above references disclose the ligands according to the present invention and the highly enantioselective transition metal catalysts derived therefrom that are useful in effecting a variety of enantioselective chemical transformations.

It is an object of the present invention to develop new chiral ligands and new chiral catalysts based on such chiral ligands that are useful in the preparation of asymmetric products via enantioselective reactions.

Accordingly, the present invention includes families of chiral ligands based on 2-amino-2'-hydroxy-1,1'-binaphthyl and related frameworks for asymmetric catalysis. Transition metal complexes of these ligands can be used as catalysts for a variety of asymmetric reactions such as hydrogenation, hydroformylation, Michael addition, Heck reaction, Aldol reaction, allylic alkylation, cyclopropanation, epoxidation, olefin metathesis and other reactions.

SUMMARY OF THE INVENTION

An optically active or racemic ligand selected from the group consisting of compounds represented by A through H; wherein A is represented by the formula selected from the group consisting of:

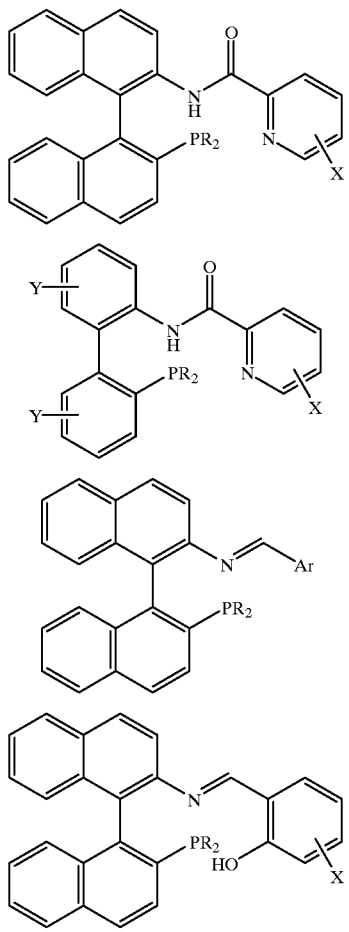

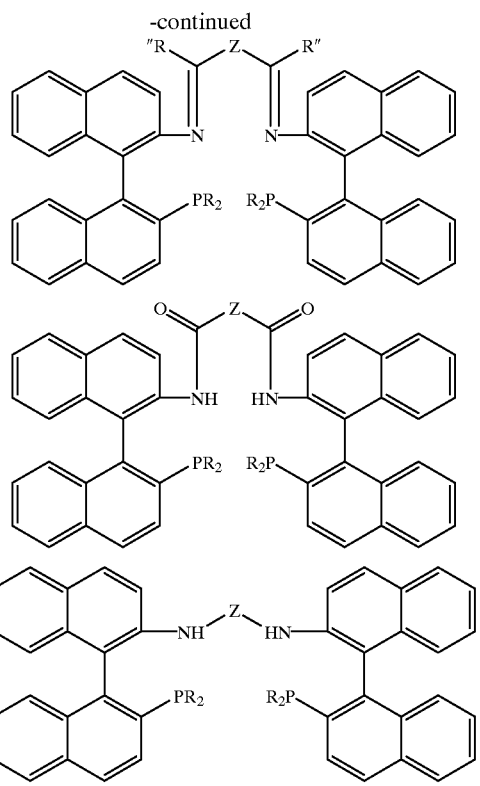

wherein each R is independently selected from the group consisting of: alkyl, aryl, substituted aryl, aralkyl and substituted aralkyl; each of X and Y is independently selected from the group consisting of: H, one or more halide, alkyl, aryl, alkoxide, nitro and carboxylate; and Ar is an aryl group;

wherein B is represented by the formula selected from the group consisting of:

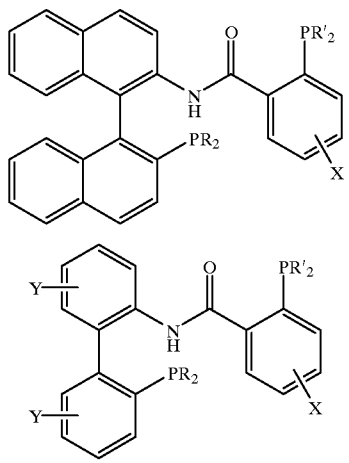

wherein each of R and R' is independently selected from the group consisting of: alkyl, aryl and aralkyl; X is independently selected from the group consisting of: H, one or more halide, alkyl, aryl, alkoxide, nitro and carboxylate; each R'' is independently selected from the group consisting of: H, alkyl, substituted alkyl, aryl, substituted aryl, 1,2-, 1,3- or 1,4-arylene, and a group that is part of an aryl system; Z is selected from the group consisting of: $(CH_2)_n$ wherein n is 0, 1 or 2, $CR_2$ wherein R is alkyl or aryl, aryl, substituted aryl, heteroaryl, phenol and aryl carboxylate;

wherein C is represented by the formula selected from the group consisting of:

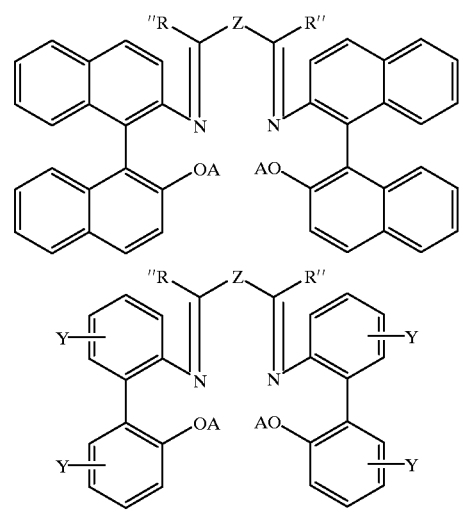

wherein each Y is independently selected from the group consisting of: H, one or more halide, alkyl, aryl, alkoxide, nitro and carboxylate; each R" is independently selected from the group consisting of: H, alkyl, substituted alkyl, aryl, substituted aryl, 1,2-, 1,3- or 1,4-arylene, and a group that is part of an aryl system; Z is selected from the group consisting of: $(CH_2)_n$ wherein n is 0, 1 or 2, $CR_2$ wherein R is alkyl or aryl, aryl, substituted aryl, heteroaryl, phenol and aryl carboxylate; and each A is independently selected from the group consisting of: H, alkyl and substituted alkyl;

wherein D is represented by the formula selected from the group consisting of:

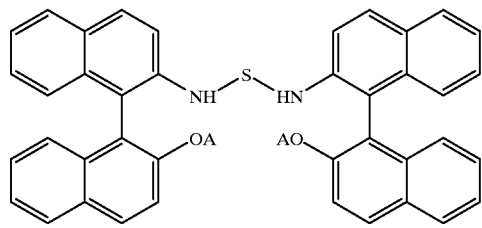

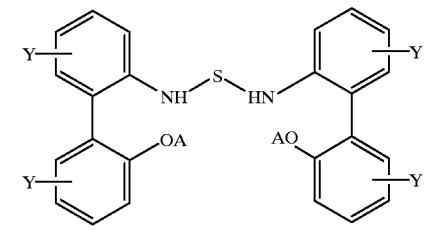

wherein each Y is independently selected from the group consisting of: H, one or more halide, alkyl, aryl, alkoxide, nitro and carboxylate; each R" is independently selected from the group consisting of: H, alkyl, substituted alkyl, aryl, substituted aryl, and a group that is part of an aryl system; S is independently selected from the group consisting of: $(CH_2)_n$ wherein n is 2–6 and $CH_2(Ar)CH_2$ wherein Ar is arylene or substituted arylene; and each A is independently selected from the group consisting of: H, alkyl and substituted alkyl;

wherein E is represented by the formula selected from the group consisting of:

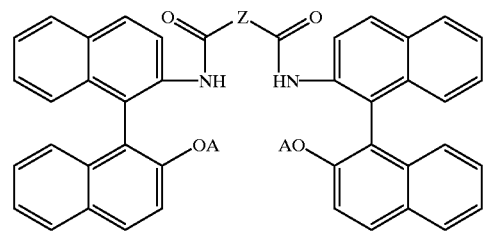

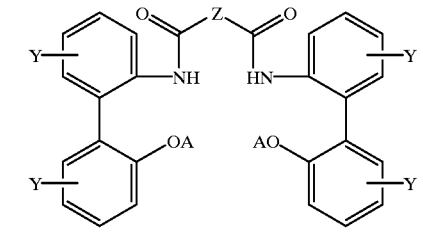

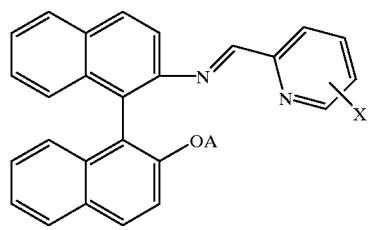

wherein each X and Y is independently selected from the group consisting of: H, one or more halide, alkyl, aryl, alkoxide, nitro and carboxylate; Z is selected from the group consisting of: $(CH_2)_n$ wherein n is 0, 1 or 2, $CR_2$ wherein R is alkyl or aryl, aryl, 1,2-, 1,3- or 1,4-arylene, substituted aryl, heteroaryl, phenol and aryl carboxylate; and each A is independently selected from the group consisting of: H, alkyl and substituted alkyl;

wherein F is represented by the formula selected from the group consisting of:

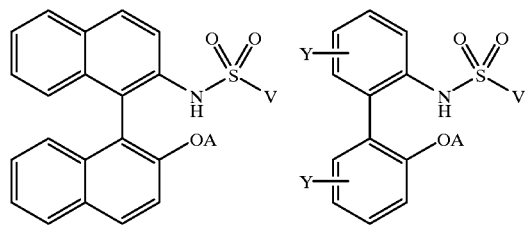

wherein each Y is independently selected from the group consisting of: H, one or more halide, alkyl, aryl, alkoxide, nitro and carboxylate; V is independently selected from the group consisting of: alkyl, aryl, substituted alkyl and substituted aryl; and A is independently selected from the group consisting of: H, alkyl and substituted alkyl;

wherein G is represented by the formula selected from the group consisting of:

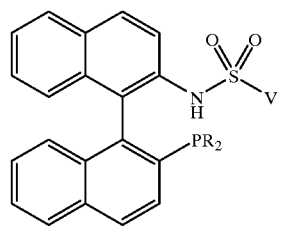

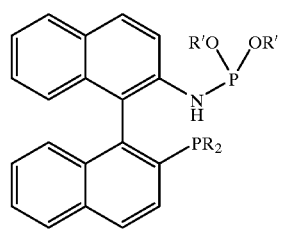

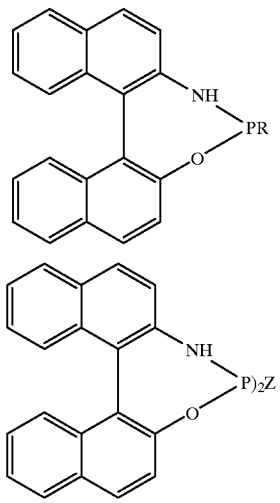

wherein V is independently selected from the group consisting of: alkyl, aryl, substituted alkyl and substituted aryl; and Z is independently selected from the group consisting of: $(CH_2)_n$, wherein n is 0, 1 or 2, $CR_2$ wherein R is alkyl or aryl, aryl, 1,2-, 1,3- or 1,4-arylene, substituted aryl, heteroaryl, phenol, ferrocene and aryl carboxylate; and wherein H is represented by the formula selected from the group consisting of:

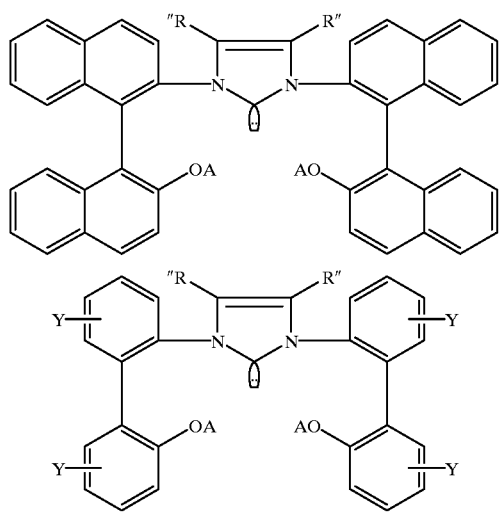

wherein each Y is independently selected from the group consisting of: H, one or more halide, alkyl, aryl, alkoxide, nitro and carboxylate; each R" is independently selected from the group consisting of: H, alkyl, substituted alkyl, aryl, substituted aryl, and a group that is part of an aryl system; and A is independently selected from the group consisting of: H, alkyl and substituted alkyl.

The present invention further includes a catalyst prepared by a process comprising contacting a transition metal salt, or a complex thereof, and a ligand according to the present invention.

The present invention still further includes a process for preparation of an asymmetric compound. The process comprises contacting a substrate capable of forming an asymmetric product by an asymmetric reaction and a catalyst according to the present invention.

The present invention also includes a process for the synthesis of chiral 2-amino-2'-hydroxy-1,1'-binaphthyl. The process comprises contacting 1,1'-bi-2-naphthol (2,2'-dihydroxy-1,1'-binaphthyl) and $(NH_4)_2SO_3H_2O$ at a temperature and length of time sufficient to produce 2-amino-2'-hydroxy-1,1'-binaphthyl.

DETAILED DESCRIPTION OF INVENTION

An array of new chiral ligands including P-P, P-N, N-N, mixed P-N, Schiff base (bidentate, tridentate, tetradentate and pentadentate), carbene are disclosed. Transition metal complexes with these ligands are effective catalysts for asymmetric hydrogenation, hydroformylation, Michael addition, Heck reaction, Aldol reaction, allylic alkylation, cyclopropanation, epoxidation, olefin metathesis and other reactions.

The ligand according to the present invention can be either of the enantiomers, which can have one or more chiral centers, or it can be a racemic or non-racemic mixture of enantiomers. Preferably, the ligand according to the present invention has an optical purity of at least 85% ee.

Applicant has discovered that enantioselective reactions can be used to prepare asymmetric products using the chiral catalysts according to the present invention, such as hydrogenation, hydroformylation, Michael addition, Heck reaction, Aldol reaction, allylic alkylation, cyclopropanation, epoxidation, and olefin metathesis.

The ligands according to the present invention have been divided into groups A through H, as shown below:

Group A can be represented by the formulas:

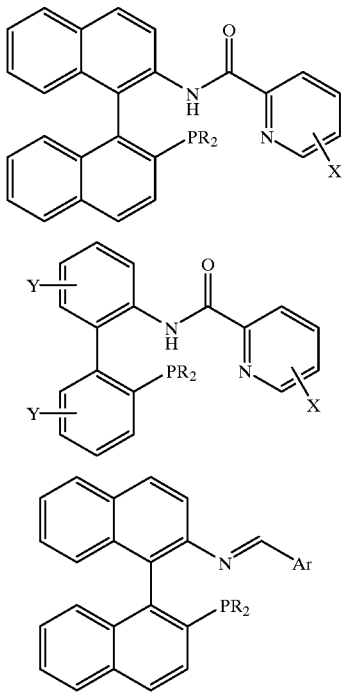

-continued

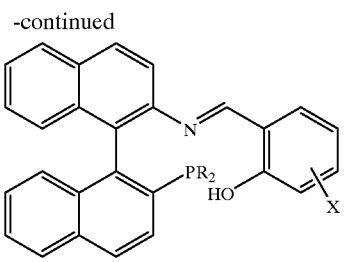

wherein each R is independently selected from the group consisting of: alkyl, aryl, substituted aryl, aralkyl and substituted aralkyl; each of X and Y is independently selected from the group consisting of: H, one or more halide, alkyl, aryl, alkoxide, nitro and carboxylate; and Ar is an aryl group.

Group B can be represented by the formulas:

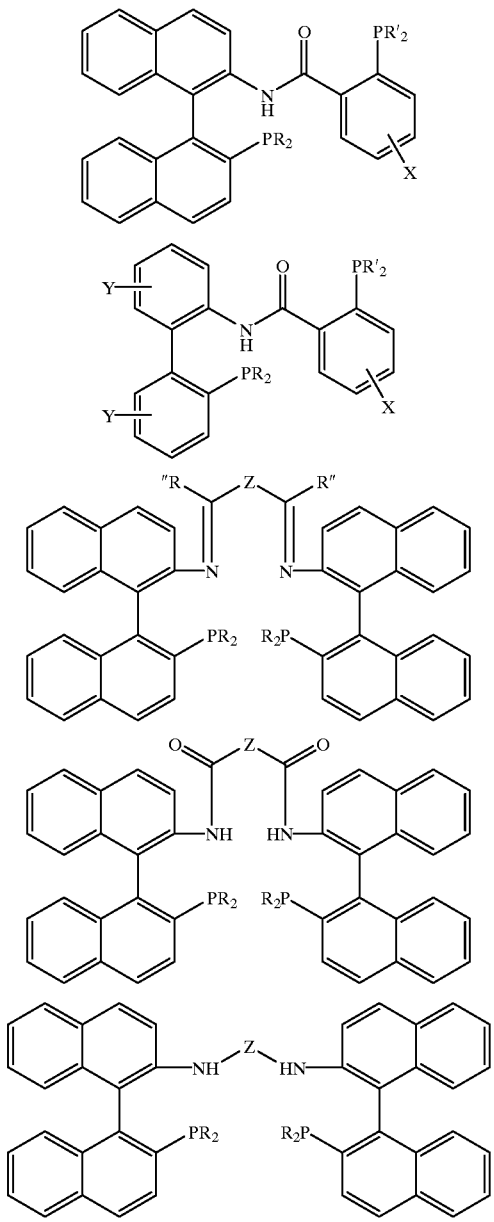

wherein each of R and R' is independently selected from the group consisting of: alkyl, aryl and aralkyl; X is independently selected from the group consisting of: H, one or more halide, alkyl, aryl, alkoxide, nitro and carboxylate; each R" is independently selected from the group consisting of: H, alkyl, substituted alkyl, aryl, substituted aryl, 1,2-, 1,3- or 1,4-arylene, and a group that is part of an aryl system; Z is selected from the group consisting of: $(CH_2)_n$ wherein n is 0, 1 or 2, $CR_2$ wherein R is alkyl or aryl, aryl, substituted aryl, heteroaryl, phenol and aryl carboxylate.

Group C can be represented by the formulas:

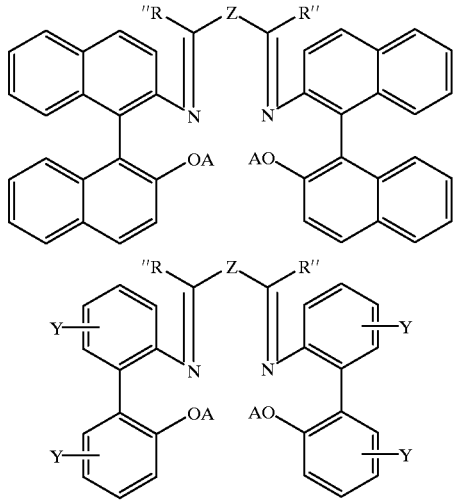

wherein each Y is independently selected from the group consisting of: H, one or more halide, alkyl, aryl, alkoxide, nitro and carboxylate; each R" is independently selected from the group consisting of: H, alkyl, substituted alkyl, aryl, substituted aryl, 1,2-, 1,3- or 1,4-arylene, and a group that is part of an aryl system; Z is selected from the group consisting of: $(CH_2)_n$ wherein n is 0, 1 or 2, $CR_2$ wherein R is alkyl or aryl, aryl, substituted aryl, heteroaryl, phenol and aryl carboxylate; and each A is independently selected from the group consisting of: H, alkyl and substituted alkyl.

Group D can be represented by the formulas:

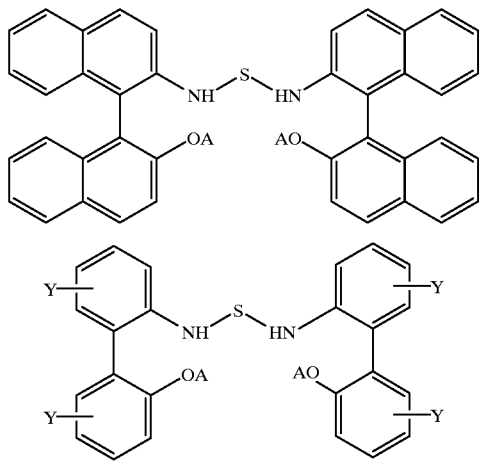

wherein each Y is independently selected from the group consisting of: H, one or more halide, alkyl, aryl, alkoxide, nitro and carboxylate; each R" is independently selected from the group consisting of: H, alkyl, substituted alkyl, aryl, substituted aryl, and a group that is part of an aryl system; S is independently selected from the group consisting of: $(CH_2)_n$ wherein n is 2–6 and $CH_2(Ar)CH_2$ wherein Ar is arylene or substituted arylene; and each A is independently selected from the group consisting of: H, alkyl and substituted alkyl;

Group E can be represented by the formulas:

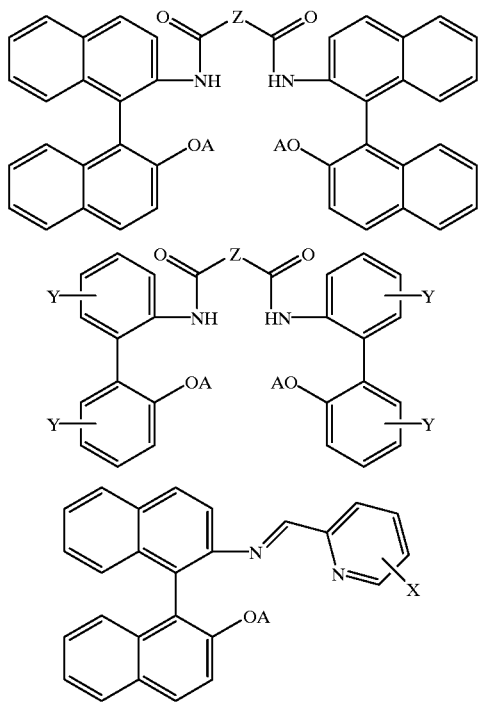

wherein each X and Y is independently selected from the group consisting of: H, one or more halide, alkyl, aryl, alkoxide, nitro and carboxylate; Z is selected from the group consisting of: $(CH_2)_n$ wherein n is 0, 1 or 2, $CR_2$ wherein R is alkyl or aryl, aryl, 1, 2-, 1,3- or 1,4-arylene, substituted aryl, heteroaryl, phenol and aryl carboxylate; and each A is independently selected from the group consisting of: H, alkyl and substituted alkyl.

Group F can be represented by the formulas:

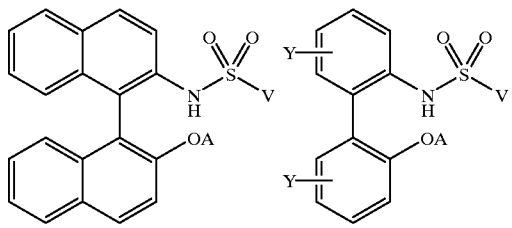

wherein each Y is independently selected from the group consisting of: H, one or more halide, alkyl, aryl, alkoxide, nitro and carboxylate; V is independently selected from the group consisting of: alkyl, aryl, substituted alkyl and substituted aryl; and A is independently selected from the group consisting of: H, alkyl and substituted alkyl;

Group G can be represented by the formulas:

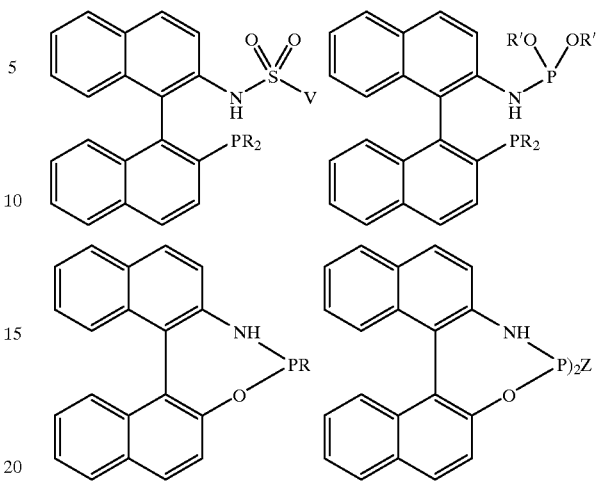

wherein V is independently selected from the group consisting of: alkyl, aryl, substituted alkyl and substituted aryl; and Z is independently selected from the group consisting of: $(CH_2)_n$ wherein n is 0, 1 or 2, $CR_2$ wherein R is alkyl or aryl, aryl, 1,2-, 1,3- or 1,4-arylene, substituted aryl, heteroaryl, phenol, ferrocene and aryl carboxylate.

Group H can be represented by the formulas:

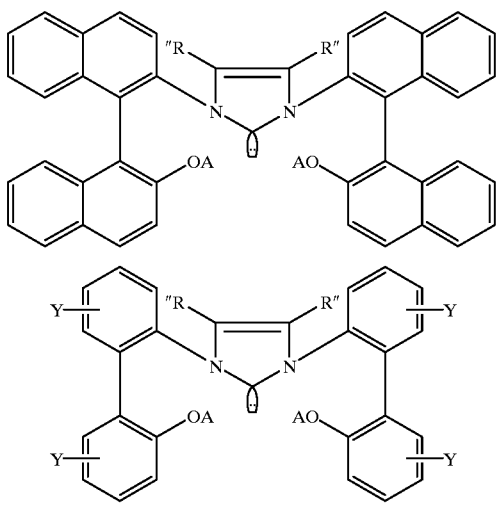

wherein each Y is independently selected from the group consisting of: H, one or more halide, alkyl, aryl, alkoxide, nitro and carboxylate; each R″ is independently selected from the group consisting of: H, alkyl, substituted alkyl, aryl, substituted aryl, and a group that is part of an aryl system; and A is independently selected from the group consisting of: H, alkyl and substituted alkyl.

Representative examples of ligands selected from each group are given below:
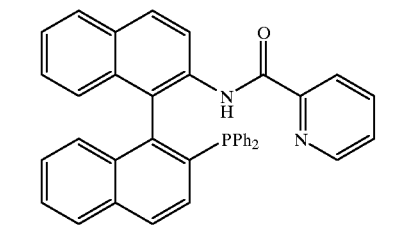
L1
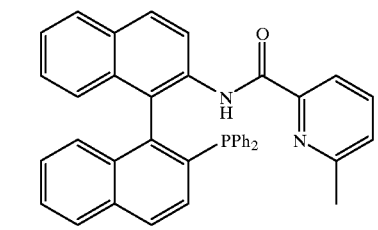
L2
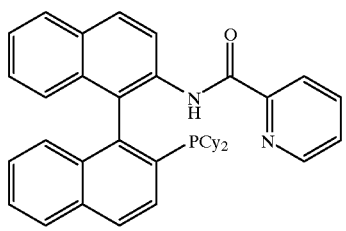
L3
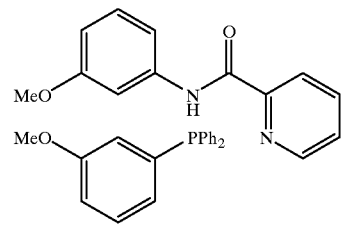
L4
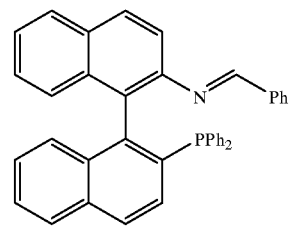
L5
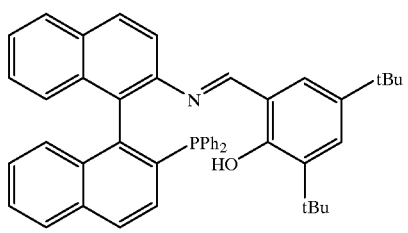
L6
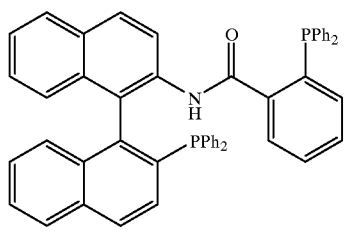
L7
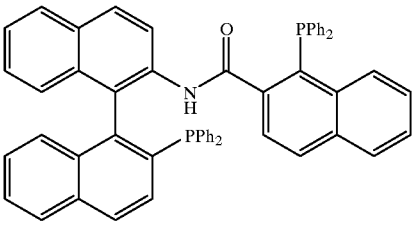
L8
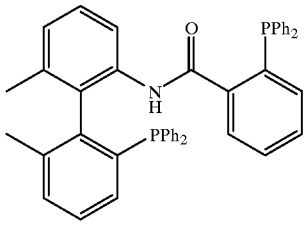
L9
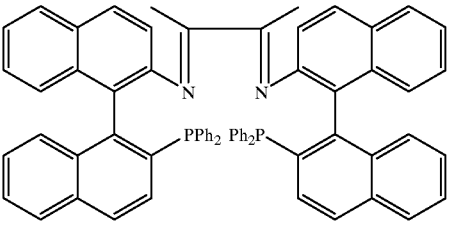
L10
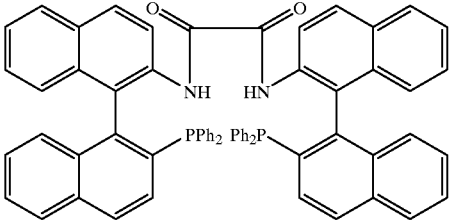
L11
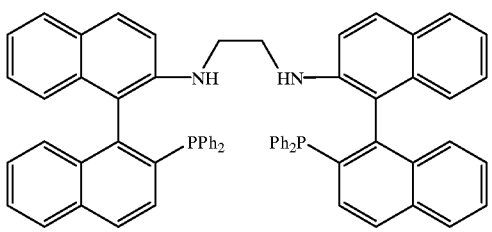
L12

L13
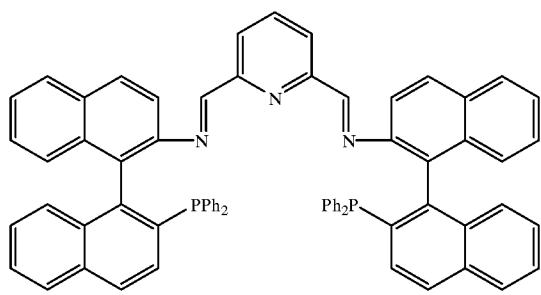
L14
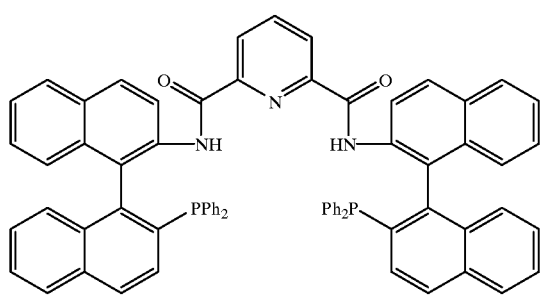
L15
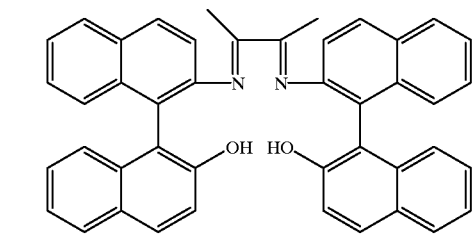
L16
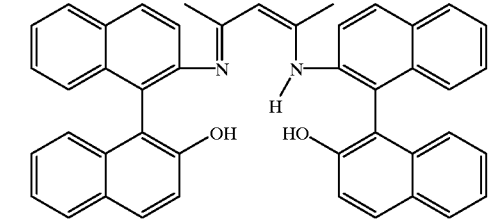
L17
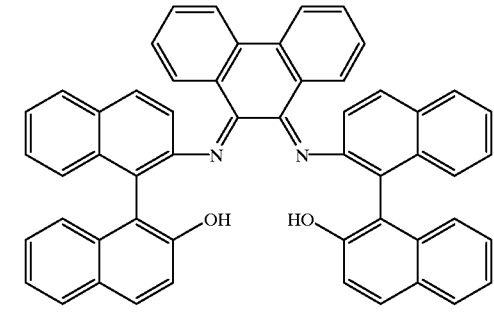
L18
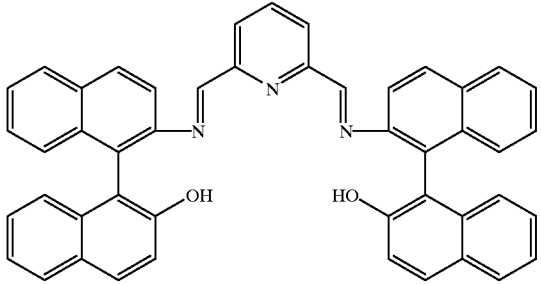
L19
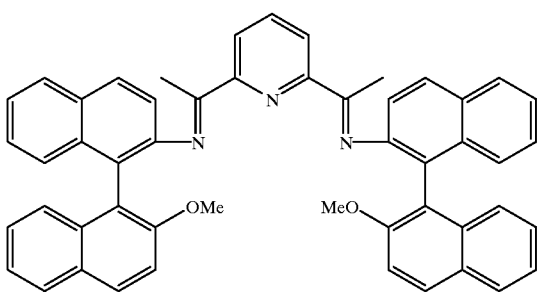
L20
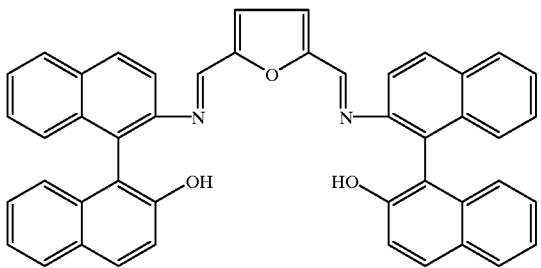
L21
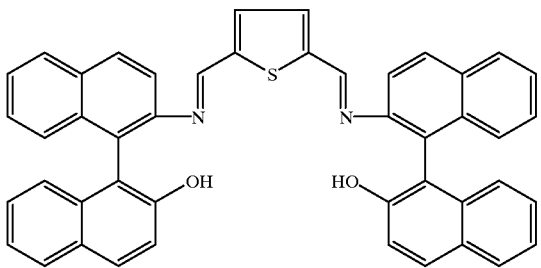
L22
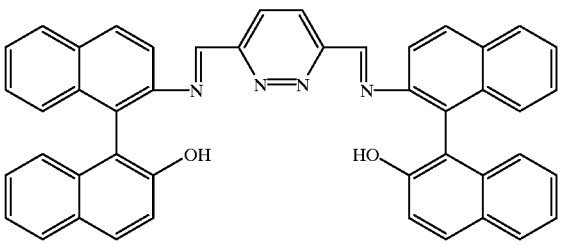

L23
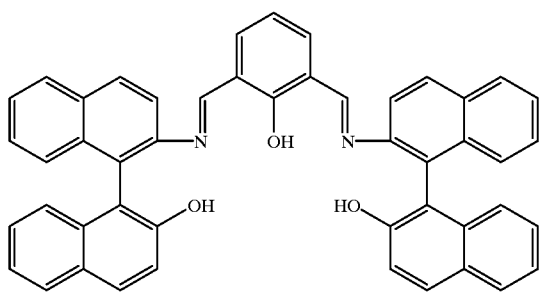
L28
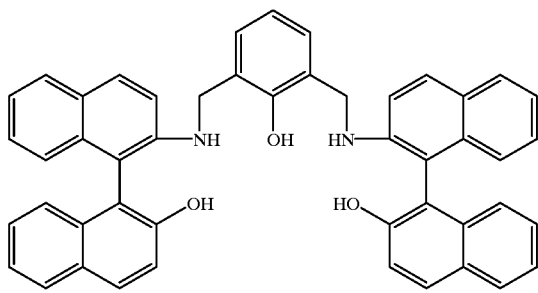
L24
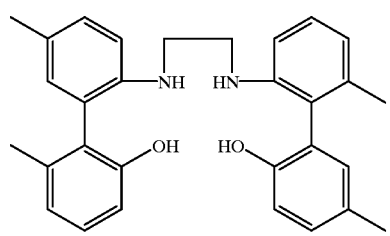
L29
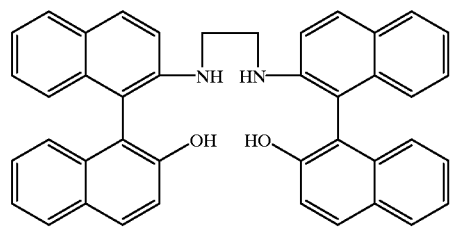
L25
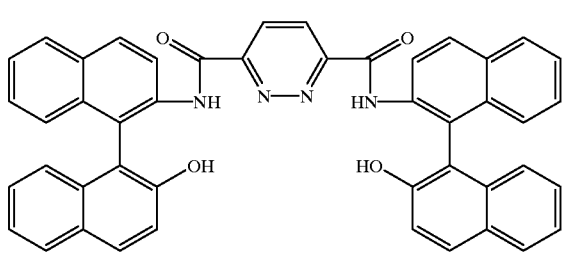
L30
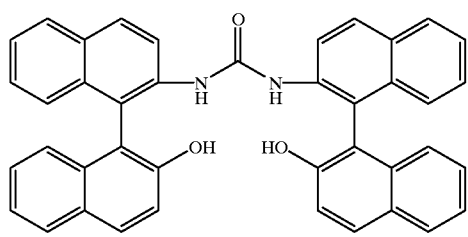
L26
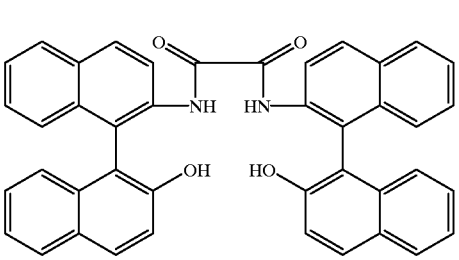
L31
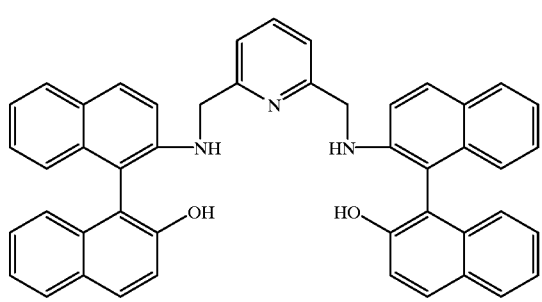
L27
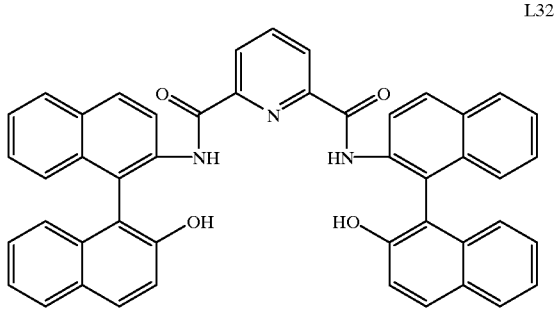
L32

-continued
L33
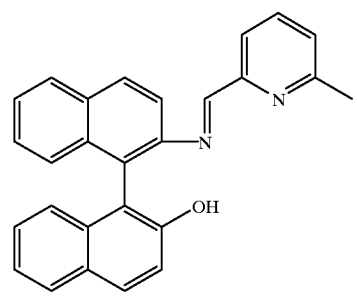
L34
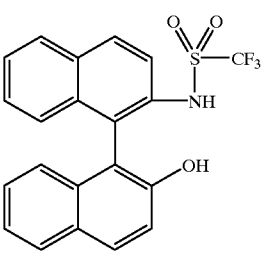
L35
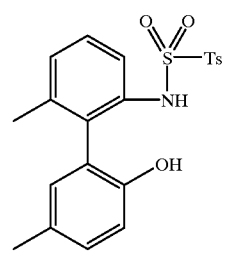
L36
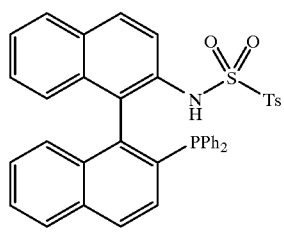
L37
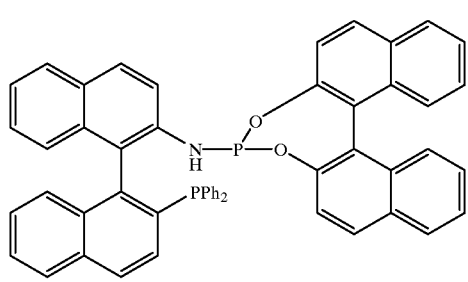
L38
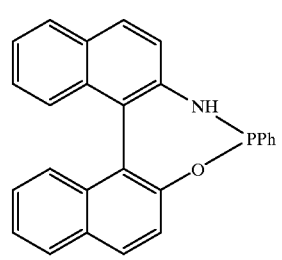
-continued
L39
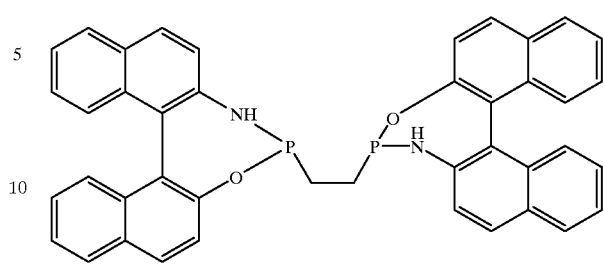
L40
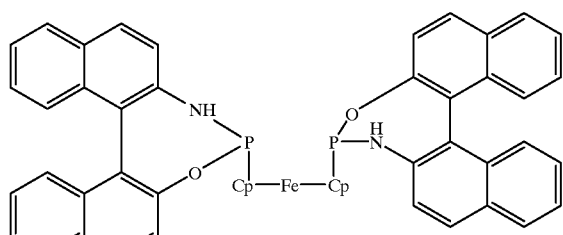
L41
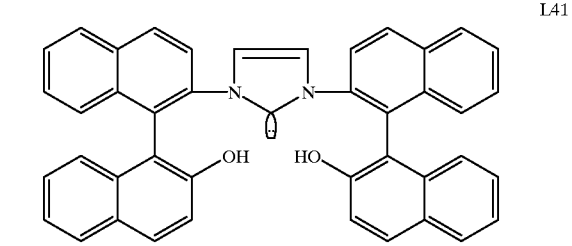
L42
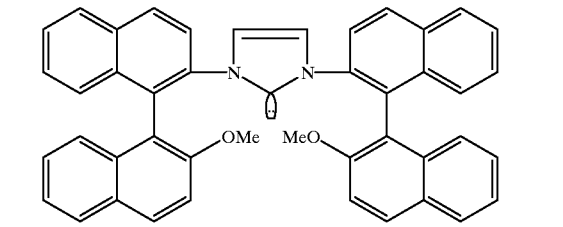
L43
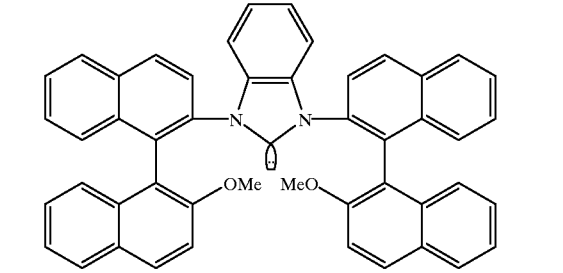
L44
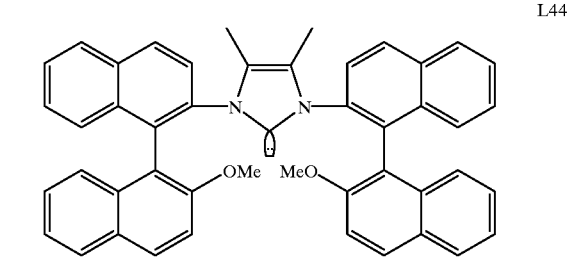

-continued

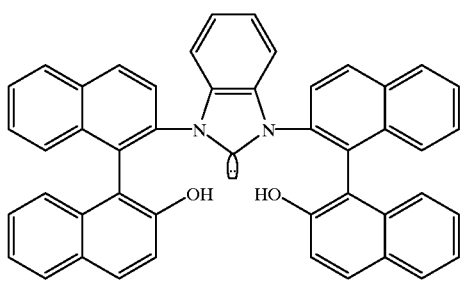

L45

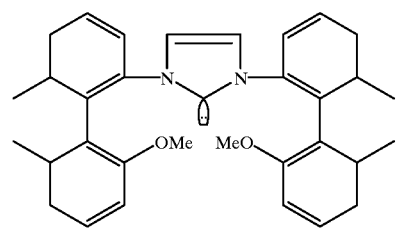

L46

Ligands designated as L1 to L14 include examples of A ligands.
Ligands designated as L1 to L14 include examples of B ligands.
Ligands designated as L5 to L24 include examples of C ligands.
Ligands designated as L25 to L35 include examples of D ligands.
Ligands designated as L25 to L35 include examples of E ligands.
Ligands designated as L25 to L35 include examples of F ligands.
Ligands designated as L36 to L46 include examples of G ligands.
Ligands designated as L36 to L46 include examples of H ligands.

Several chiral ligands (L1, L2, L18, L26, L27, L32, L33 and others) have been prepared and tested for transition metal-catalyzed asymmetric reactions. It has been found that Cu-L1 and Cu-L2 complexes of the present invention are particularly useful in asymmetric Michael addition reactions, whereas Cu-L33 has been found to be particularly useful in asymmetric cyclopropanation reactions. Ru-L18 has been found to be particularly useful as well in asymmetric cyclopropanation reactions.

The present invention further includes a catalyst prepared by a process comprising contacting a transition metal salt, or a complex thereof, and a ligand according to the present invention.

Preferably, the catalyst has an optical purity of at least 85% ee.

The preferred transition metals for preparing the catalysts of the present invention include Pd, Rh, Ru, Ir, Cu, Ni, Mo, Ti, V, Re and Mn. Preferably, the transition metal, metal salt, or complex thereof, from which the catalyst is prepared include palladium, rhodium, ruthenium, iridium, copper, nickel, molybdenum, titanium, vanadium, rhenium and manganese. Examples of such transition metals include $Pd_2(DBA)_3$; $Pd(OAc)_2$; $[Rh(COD)Cl]_2$; $[Rh(COD)_2]X$; $Rh(acac)(CO)_2$; $RuCl_2(COD)$; $RuCl_2(=CHR)(PR'_3)_2$; $Ru(COD)(methylallyl)_2$; $Ru(ArH)Cl_2$; $[Ir(COD)_2Cl]_2$; $[Ir(COD)_2]X$; $Cu(OTf)$; $Cu(OTf)_2$; $Cu(Ar)X$; $CuX$; $NiX_2$; $MoO_2(acac)_2$; $Ti(OiPr)_4$; $VO(acac)_2$; $MeReO_3$; $MnX_2$ and $Mn(acac)_2$; wherein each R and R' is independently alkyl or aryl; Ar is an aryl group; and X is a counteranion.

The catalyst can be prepared as an isolated compound or it can be generated in situ prior to reaction.

The present invention still further includes a process for preparation of an asymmetric compound. The process comprises contacting a substrate capable of forming an asymmetric product by an asymmetric reaction and a catalyst according to the present invention.

The asymmetric reaction can be any reaction. Preferably, the asymmetric reaction is reaction, such as, hydrogenation, hydroformylation, allylic alkylation, cyclopropanation, Heck reaction, Aldol reaction, Michael addition and epoxidation.

Preferably, when the asymmetric reaction asymmetric reaction is hydrogenation, the substrate can be a ketone, an imine and an alkane; and preferably, the catalyst is prepared by contacting a Rh, Ru or Ir salt, or a complex thereof, and the ligand is selected from group A, group B or group G ligands.

Preferably, when the asymmetric reaction asymmetric reaction is allylic alkylation or Heck reaction, the substrate is an ethylenically unsaturated compound; and the catalyst is prepared by contacting a Pd salt, or a complex thereof, and the ligand is also selected from group A, group B or group G ligands.

Preferably, when the asymmetric reaction asymmetric reaction is hydroformylation, the substrate is an ethylenically unsaturated compound; and the catalyst is prepared by contacting a Rh salt, or a complex thereof, and a ligand is similarly selected from group A, group B or group G ligands.

Preferably, when the asymmetric reaction is epoxidation, the substrate is an ethylenically unsaturated compound; and the catalyst is prepared by contacting a Ti, V, Mo, Re or Mn salt, or a complex thereof, and the ligand is selected from group C, group D, group E or group F ligands.

Preferably, when the asymmetric reaction is Michael addition, the substrate is an ethylenically unsaturated compound; and the catalyst is prepared by contacting a Cu or Ni salt, or a complex thereof, and the ligand is selected from group A, group B, or group G ligands.

Preferably, when the asymmetric reaction is cyclopropanation, the substrate is an ethylenically unsaturated compound; and the catalyst is prepared by contacting a Cu or Ru salt, or a complex thereof, and the ligand is selected from group E ligands.

Preferably, when the asymmetric reaction is a Heck reaction, the substrate is an ethylenically unsaturated compound; and the catalyst is prepared by contacting a Pd salt, or a complex thereof, and the ligand is selected from group H ligands.

Because many of the ligands of the present invention employ 2-amino-2'-hydroxy-1,1-binaphthyl (NOBIN), or a derivative thereof, as the starting material, a practical method of synthesizing 2-amino-2'-hydroxy-1,1'-binaphthyl (NOBIN) was realized from BINOL through a single step.

The facile purification procedure makes this process amenable to large-scale synthesis of NOBIN. Chiral 2-amino-2'-hydroxy,-1,1'-binaphthyl (NOBIN) developed by Kocovsky has proven to be an excellent framework for constructing chiral ligands. 2-naphthylamine is prepared in high yield from 2-naphthol via the Bucherer reaction. NOBIN may also be synthesized from BINOL in a similar way.

Although it is reported that 2-naphthylamine can be obtained in high yield when 2-naphthol was heated to 150° C. in the presence of concentrated aqueous ammonia and ammonium sulfite for 8 hours, no reaction was observed when the same conditions were subjected to BINOL. When the temperature was increased to 200° C. and more ammonium sulfite was employed, NOBIN was exclusively formed without detectable amounts of BINAM. Thus, by extending the reaction time to 5 days and increasing the amount of ammonium sulfite to 10 equivalents, the starting material disappeared completely. The produced solid was simply filtered and washed with water. A 91% isolated yield of NOBIN was obtained by recrystallization from benzene. Thus, a practical procedure for the synthesis of NOBIN from BINOL in a single-step via a process that can be scaled-up in high yield is provided.

Accordingly, the present invention includes a process for the synthesis of chiral 2-amino-2'-hydroxy-1,1'-binaphthyl (NOBIN). The process comprises contacting 1,1'-bi-2-naphthol (2,2'-dihydroxy-1,1'-binaphthyl) and $(NH_4)_2SO_3.H_2O$ at a temperature and length of time sufficient to produce 2-amino-2'-hydroxy-1,1'-binaphthyl.

The detailed description of ligand synthesis and asymmetric reactions thereof is provided below.

Synthesis of NOBIN and its Derivatives

A. General Procedures:

Column chromatography was performed using EM Silica gel 60 (230–400 mesh). $^1H$, $^{13}C$ and $^{31}P$ NMR were recorded on Bruker AM-300, and AMX-360 spectrometers. Chemical shifts were reported in ppm down field from tetramethylsilane with the solvent resonance as the internal standard. Optical rotation was obtained on a Perkin-Elmer 241 polarimeter. MS spectra were recorded on a KRATOS mass spectrometer MS 9/50 for LR-EI and HR-EI. GC analysis was carried on Helwett-Packard 6890 gas chromatography using chiral capillary column. HPLC analysis was carried on Waters™ 600 chromatography.

B. Materials:

THF, diethylether, hexanes, toluene and benzene were dried and distilled from sodium/benzophenone ketyl under nitrogen before use. Dichloromethane and 1,2-dichloroethane were distilled from $CaH_2$ and sealed under $N_2$ in Aldrich sure seal bottles. All chemicals were purchased from Aldrich, except 6-methylpyridine-2-carboxylic acid from TCI, 3,5-di-tert-butyl-2-hydroxybenzaldehyde from Lancaster.

I. NOBIN Synthesis

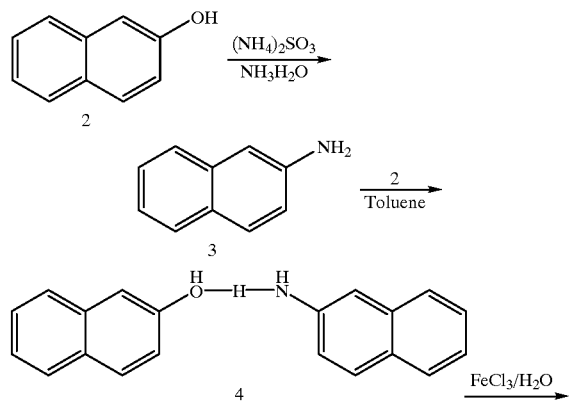

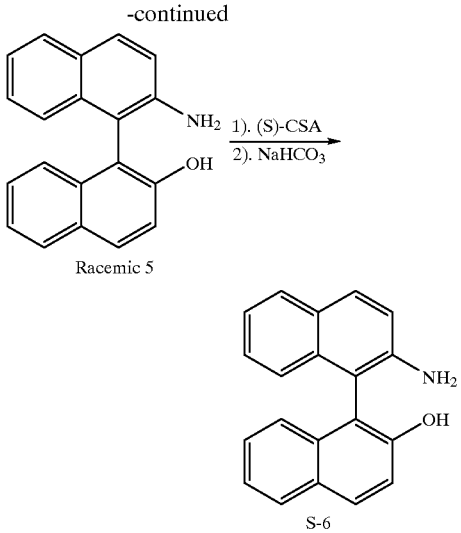

2-Amino-naphthalene (3):

To a 300 mL autoclave was added 36.5 g of 2-naphthol (2, 0.253 mol), 34.0 g of $(NH_4)_2SO_3.H_2O$ (0.254 mol) and 85 mL of concentrated aqueous ammonia, the mixture was heated to 150° C. with an oil-bath for 10 h. The pressure was built to about 10 atm at 150° C. and then cooled to room temperature while stirring. The solid was filtered, washed with water, and dissolved in a mixture of 70 mL of concentrated hydrochloric acid, 300 mL of ethanol and 200 mL of water at 70° C. The solution was treated with 5 g of activated charcoal for 0.5 h at 70° C. and filtered. The impurity in the filtrate was extracted with 200 mL of toluene and discarded. The aqueous phase was cooled to room temperature and neutralized with 90 mL of concentrated aqueous ammonia. The mixture was extracted with toluene (2×400 mL) at 70° C. The toluene layer was washed with water (2×100 mL), and degassed under $N_2$ for 5 min. The small amount of water in toluene was removed by refluxing with a Dean-Stark trap, and concentrated to obtain the crude product. The crude product was recrystallized from 200 mL of degassed toluene to afford 26.9 g of 3, the second crop from the mother liquid was 2.4 g. Yield: 29.3 g (80%): mp 106–108° C., $^1H$ NMR $(CDCl_3)$ _4.07 (s, 2H ), 7.19–7.24 (m, 2H), 7.47–7.52 (m, 1H), 7.61–7.66 (m, 1H), 7.85–7.97 (m, 3H), $^{13}C$ NMR $(CDCl_3)$ _108.5, 118.2, 122.4, 125.8, 126.3, 127.7, 127.9, 129.2, 134.9, 144.0.

Formation of Molecular Crystal of 2-amino-naphthalene and 2-naphthol (4):

Molecular crystal 4 was prepared by a modified procedure according to the literature procedure (Ding, K.; Xu, Q.; Wang, Y.; Liu, J.; Yu, Z.; Du, B.; Wu, Y.; Koshima, H. and Matsuura, T.; Chem. Commun. 1997, 693). To a mixture of 1.44 g of 2-naphthol (10 mmol) and 1.43 g of 3 (10 mmol) in a 50 mL round flask was added 10 mL of dried toluene under $N_2$ atmosphere. The mixture was heated to a clear solution, then cooled to room temperature to afford 2.40 g of the "molecular crystal" and 0.40 g of product recovered from mother liquid as the second crop after evaporation of the solvent. Yield: 2.80 g (97.6%). This product can be used in next step without further purification. The sample using for the melting point determination was recrystallized from toluene. mp 127–128° C.

Racemic 2-amino-2'-hydroxy-1,1'-binaphthyl (NOBIN, 5):

To a stirred solution of 81 g of iron (III) chloride hexahydrate (0.3 mol) in 400 mL of degassed water, was added 23 g of 4 (0.08 mol). The resulting suspension was purged with nitrogen for 20 min, placed into a preheated 55° C. oil bath, and stirred for 6 h. The mixture was then cooled to room temperature and filtered. The filter cake was washed with water until colorless. The residue was dried in an oven overnight at 80° C. to give 22.5 g black solid. The solid was then dissolved in 1000 mL of acetone and the solution was loaded on a silica gel plug (50 g) with 20 g of activated charcoal on the top. Another 1000 mL of acetone was used to elute the compound. The resulting solution was concentrated under vacuum. The solid residue was dissolved in a mixture of 40 mL of concentrated hydrochloric acid and 300 mL of ethanol, then diluted with 100 mL of water. The impurities in the solution (mainly 2,2'-binol by TLC analysis) was extracted with 3×200 mL of toluene and discarded. To the aqueous layer was added 100 g of ice and then 60 mL of concentrated aqueous ammonia to precipitate the crude NOBIN 5. The crude 5 (12.4 g) obtained on filtration was dried at 80° C. overnight in an oven. Recrystallization of this crude product from 500 mL of toluene gave 11.2 g (48.7%) of pure 5, mp: 236–237° C.; $^1$H NMR (CD$_3$COCD$_3$) _4.43 (s, 2H), 6.88–6.90 (d, J=7.0 Hz, 1H), 7.06–7.13 (m, 3H), 7.21–7.28 (m, 3H), 7.34–7.37 (d, J=8.8 Hz, 1H), 7.65 (s, 1H), 7.75–7.77 (m, 2H), 7.87–7.94 (m, 2H); FAB-MS m/z 285.2 (M+H)$^+$.

S-2-Amino-2'-hydroxy-1,1'-binaphthyl (NOBIN, 6):

In a 2 L flask with a magnetic stir bar was added 10 g of racemic NOBIN 5 (35.1 mmol), 600 mL of toluene and 200 mL of isopropanol. The suspension was stirred and heated to 60° C., and 8.55 g of (S)-camphor-10-sulfonic acid (CSA) (36.9 mmol) was added. A clear solution was obtained quickly (within 1 min) after the addition of the CSA. The solution was stirred for 1 h while the temperature was maintained between 60° C. to 65° C. The precipitate began to appear about 20 min after CSA was added. The mixture was gradually cooled to room temperature and stirred overnight. The precipitate solid was obtained by filtration, washed twice with 20 mL of toluene, and then 20 mL of hexanes. After drying with air, 6.95 g (76.6%) of solid was collected. The solid was placed into a 500 mL separation funnel and treated with 300 mL of CH$_2$Cl$_2$ and 50 mL of saturated NaHCO$_3$ solution. The organic phase was separated and washed with 50 mL of brine and dried over anhydrous Na$_2$SO$_4$ and concentrated in vacuo to give 3.75 g (75%) crude product. Recrystallization of this crude product from 55 mL of dried benzene (15 mL of benzene/1.0 g of crude product) afforded pure 6, which was dried under vacuum in an oil-bath at 100° C. for 2 h (3.45 g, 69%) (optical purity of >99% ee by HPLC, 1.0 mL/min, 2-PrOH/Hexanes=20/80, Chiralcel OD, $t_S$=25.73 min, $t_R$ unseen, while $t_R$=29.53 min for racemic NOBIN). mp 168–169° C., $[\alpha]_D^{25}$ –123.3 (c 1.04, THF).

II. Bidentate Ligand Synthesis

1. Preparation of S-(+)-2-Amino-2'-(diphenylphosphino)-1,1'-binaphthyl:

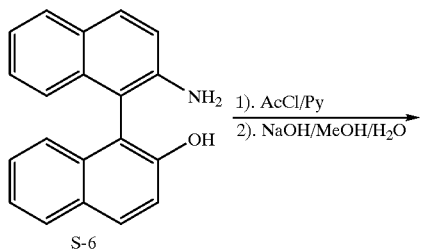

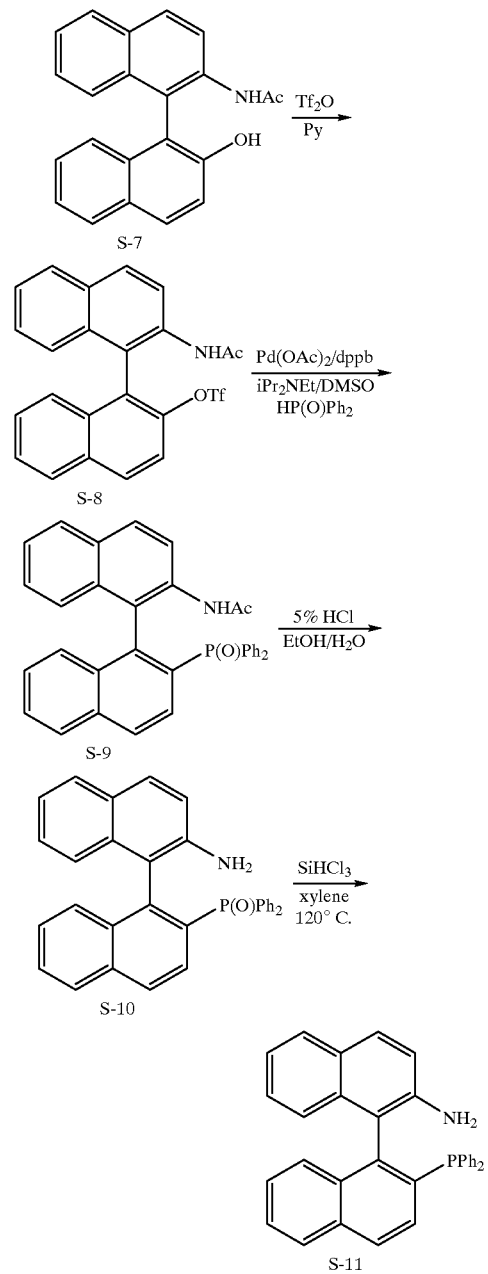

S-2-(Acetamido)-2'-hydroxy-1,1'-binaphthyl (7):

In a 100 mL flask, 2.0 mL of acetyl chloride (13.75 mmol) was slowly added to a solution of 3.28 g of 6 (11.5 mmol) in 50 mL of dried CH$_2$Cl$_2$ and 5 mL of dried Et$_3$N at 0° C. The mixture was stirred at room temperature for 6 h. After passing through a silica gel plug (40 g) to remove salts, the CH$_2$Cl$_2$ solution was concentrated to dryness to afford crude N,O-diacetate of 6. The solid was dissolved in a NaOH (2 g) solution in 300 mL of MeOH and 20 mL of water. The solution was stirred at room temperature for 1 h and TLC showed that the N,O-diacetate of 6 was totally consumed. After removal of MeOH under vacuum, 50 mL of saturated NH$_4$Cl and 50 mL of water were added. The aqueous layer was extracted by CH$_2$Cl$_2$ (3×100 mL). The combined CH$_2$Cl$_2$ layer was washed with 50 mL of saturated NaHCO$_3$, 50 mL of water and 50 mL of brine and dried over anhydrous Na$_2$SO$_4$. The crude product was obtained through filtration and was purified by a silica gel column (50 g) eluted with 1:1 hexanes/EtOAc to afford 3.32 g (87.7%) of 7. mp: 207–208° C. $[\alpha]_D^{25}$ −81.5 (c 1.0, CHCl$_3$), $^1$H NMR (CDCl$_3$) 1.83 (s, 3H), 6.91 (s, 1H), 7.01 (d, J=8.4 Hz, 1H), 7.15 (d, J=8.5 Hz, 1H), 7.27–7.31 (m, 2H), 7.35–7.47 (m, 3H), 7.92 (t, J=7.0 Hz, 2H), 7.98 (d, J=8.9 Hz, 1H ), 8.04 (d, J=9.1 Hz, 1H), 8.54 (d, J=8.8 Hz, 1H); FAB-MS m/z 328.2 (M+H)$^+$.

S-2-(Acetamido)-2'-(trifluoromathanesulfonnyloxy)-1,1'-binaphthyl (8):

2.0 mL of trifluoromethanesulfonic anhydride (, 11.89 mmol) was slowly added to a solution of 2.72 g of 7 (8.32 mmol) in 40 mL of CH$_2$Cl$_2$ and 5 mL of 2,6-lutidine (43 mmol) at 0° C., and the mixture was stirred for 0.5 h at 0° C. The solution was then gradually warmed to room temperature and stirred overnight. The reaction mixture was poured into 50 g of ice. The aqueous phase was extracted with 2×50 mL of CH$_2$Cl$_2$. The combined organic phase was washed with 2×20 mL of 5% HCl, 20 mL of saturated NaHCO$_3$ and 20 mL of water. The solution was dried over anhydrous Na$_2$SO$_4$ and concentrated under vacuum. The residue was loaded on a silica gel column (50 g) and eluted with CH$_2$Cl$_2$ to give 3.33 g (87%) of foamy solid, mp: 68–70° C. $[\alpha]_D^{25}$ −30.0 (c 1.0, THF), $^1$H NMR (CD$_3$COCD$_3$) 1.74 (s, 3H), 6.92 (d, J=8.5 Hz, 1H), 7.23–7.30 (m, 2H), 7.41–7.49 (m, 2H), 7.63–7.68 (m, 1H), 7.73 (d, J=9.1 Hz, 1H), 7.99 (d, J=8.1 Hz, 1H), 8.08–8.11 (m, 2H), 8.17 (d, J=8.3 Hz, 1H), 8.33 (d, J=9.1 Hz, 1H), 8.42 (d, J=8.8 Hz, 1H); FAB-MS m/z 460.2 (M+H)$^+$.

S-2-(Acetamido)-2'-(diphenylphosphinoyl)-1,1'-binaphthyl (9):

To a mixture of 3.32 g of 8 (7.26 mmol), 3.40 g of the diphenylphosphine oxide (16.8 mmol), 338 mg of palladium (II) acetate (1.51 mmol), and 647 mg of 1,4-bis (diphenylphosphino) butane (dppb, 1.52 mmol) were added 150 mL of dimethyl sulfoxide and 5.0 mL of diisopropyl-ethylamine (3.71 g, 28.8 mmol), and the mixture was stirred at 120° C. for 8 h. After cooling to room temperature, the reaction mixture was poured into 900 mL of 5% aqueous HCl and the product was extracted with CH$_2$Cl$_2$ (3×150 mL). The combined organic layer was washed twice with 100 mL of 1% aqueous HCl, 100 ml of saturated NaHCO$_3$ solution, 100 mL of water, dried over anhydrous Na$_2$SO$_4$, and concentrated under reduced pressure. The residue was loaded on a column (200 g silica gel and 20 g of activated charcoal) and eluted with dichloromethane: ethyl acetate (1:1) to afford 2.88 g (78%) of 9 as a light yellow solid after recrystallization from dichloromethane and hexanes. $[\alpha]_D^{25}$+193.8 (c 1.0, THF), $^1$H NMR (CDCl$_3$) δ 1.90 (s, 3H), 6.50 (d, J=8.4 Hz, 1H), 6.59–6.64 (m, 2H), 6.73–6.78 (m, 1H), 6.92–6.96 (m, 1H), 7.09–7.23 (m, 5H), 7.47–7.57 (m, 7H), 7.62–7.71 (m, 2H), 7.87–7.97 (m, 4H), $^{31}$P NMR δ 28.65 (s), S-(+)-2-Amino-2'-(diphenylphosphinoyl)-1,1'-binaphthyl (10):

2.88 g (5.64 mmol) of 9 was suspended in 100 mL of EtOH and 20 mL of 5% aqueous HCl. The mixture was heated at reflux for 12 h to form a light yellow solution. After cooling to room temperature, 50 mL of water was added to dilute the solution. After removal of EtOH under reduced pressure, 20 mL of concentrated aqueous ammonia was added to neutralize the solution. The mixture was extracted with dichloromethane (2×50 mL). The combined organic layer was washed with 20 mL of NH$_4$Cl, 20 mL of saturated NaHCO$_3$ solution and 20 mL of brine. This solution was dried over anhydrous Na$_2$SO$_4$ and concentrated under reduced pressure. The residue was loaded on a silica gel column (120 g) and eluted with dichloromethane : triethy-lamine (10:1) to afford 2.53 g (96%) of 10 as a yellow solid. mp 131–134° C. $[\alpha]_D^{25}$+173.9 (c 1.22, THF), $^1$H NMR (CD$_2$Cl$_2$) δ 3.87 (bs, 2H), 6.48 (d, J=8.4 Hz, 1H), 6.87–6.91 (m, 4H), 7.01–7.05 (m, 2H), 7.16 (d, J=8.6 Hz, 1H), 7.24–7.30 (m, 3H), 7.39–7.43 (m, 2H), 7.47–7.52 (m, 3H), 7.57 (t, J=7.5 Hz, 1H), 7.63–7.73 (m, 3H), 7.96–8.00 (m, 2H), $^{13}$C NMR δ 115.55, 115.61, 119.03, 122.03, 124.79, 126.11, 127.11, 127.56, 127.70, 127.84, 127.86, 128.24, 128.38, 128.46, 128.49, 128.59, 128.63, 129.30, 129.44, 130.14, 130.64, 130.67, 130.72, 130.82, 131.40, 131.45, 131.68, 131.71, 132.01, 132.11, 132.55, 132.58, 133.29, 133.45, 133.58, 134.43, 135.72, 135.74, 141.73, 141.83, 144.44, $^{31}$P NMR δ 26.54 (s), HRMS calculated for C$_{32}$H$_{24}$NP (M+1): 470.1642; found: 470.1674.

S-(+)-2-Amino-2'-(diphenylphosphino)-1,1'-binaphthyl (11):

3.0 mL of trichlorosilane (4.0 g, 29.8 mmol) was added to a mixture of 1.01 g of 10 (2.15 mmol) and 5.0 mL of triethylamine (3.63 g, 3.59 mmol) in 80 mL of p-xylene at ice-bath. The mixture was stirred at 0° C. for 0.5 h and then heated to 120° C. for 5 h. After cooling to room temperature, 100 mL of dichloromethane and 10 mL of saturated NaHCO$_3$ solution were added to the reaction mixture. The resulting suspension was stirred for 0.5 h and filtered through a Celite. The solid residue was extracted with dichloromethane and washed with water. The combined organic layer was dried over anhydrous Na$_2$SO$_4$ and concentrated under reduced pressure. The resulting solution was loaded on a silica gel column (50 g) and eluted with CH$_2$Cl$_2$ to afford 700 mg (72%) of 11 as a white solid. $[\alpha]_D^{25}$+28.1 (c 1.0, THF), $^1$H NMR (CDCl$_3$) δ 3,22 (bs, 2H), 6.75 (d, J=8.4 Hz, 1H), 7.00–7.07 (m, 2H), 7.13–7.25 (m, 6H), 7.34–7.41 (m, 7H), 7.52–7.56 (m, 2H), 7.79 (d, J=8.1 Hz, 1H), 7.85 (d, J=8.7 Hz, 1H), 7.95 (d, J=8.3 Hz, 2H), $^{31}$P NMR δ −13.43 (s), FAB-MS m/z 453.1 M$^+$.

2. Preparation of P,N-bidentate Ligands 1a and 1b:

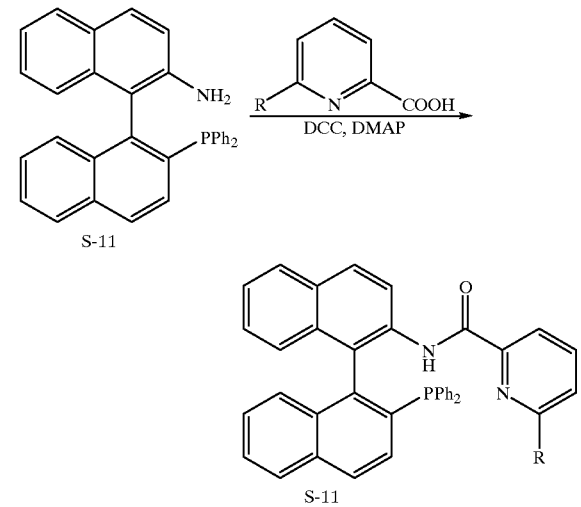

1a (R = H)
1b (R = CH$_3$)

S-(+)-2-(2-pyridinylcarboxamido)-2'-(diphenylphosphino)-1,1'-binaphthyl (1a):

To 0.863 g of 11 (1.91 mmol) in 50 mL of CH$_2$Cl$_2$, 0.940 g of 2-pyridine carboxylic acid (7.64 mmol), 20 mg of 4-N,N-dimethylamino-pyridine (DMAP) (0.164 mmol) and 2.06 g of 1,3-dicyclohexylcarbodiimide (DCC, 10 mmol) were added. The mixture was stirred overnight at rt. To this mixture, 20 mL of water and 0.2 mL of ACOH were added.

After stirring the mixture for 2 h at room temperature, the solid residue was filtered and washed with 10 mL of CH$_2$Cl$_2$. The organic phase was separated from the aqueous layer in a separating funnel, dried over anhydrous Na$_2$SO$_4$, and concentrated under reduced pressure. The residue was loaded with a silica gel column (80 g) and eluted with hexanes: CH$_2$Cl$_2$ (1:2) to afford 906 mg (85%) of 1a as a white solid. mp: 185–187° C. [α]$_D^{25}$+45.6 (c 1.0, CHCl$_3$), $^1$H NMR (CD$_2$Cl$_2$) _6.87 (d, J=8.4 Hz, 1H ), 6.93–6.98 (m, 2H), 7.03–7.35 (m, 13H), 7.49–7.53 (m, 2H), 7.76–7.81 (m, 1H), 7.91–8.09 (m, 6H), 8.87 (d, J=9.0 Hz, 1H), 9.75 (s, 1H), $^{13}$C NMR _120.15, 122.70, 125.11, 125.23, 125.36, 126.54, 126.73, 126.76, 126.88, 127.05, 127.78, 127.96, 128.67, 128.76, 128.85, 128.96, 128.98, 129.04, 129.18, 129.75, 129.89, 131.13, 131.15, 131.27, 133.55, 133.65, 134.02, 134.05, 134.11, 134.16, 134.38, 134.43, 134.89, 135.50, 135.53, 137.45, 137.61, 137.65, 137.82, 138.17, 138.20, 138.37, 140.62, 141.08, 148.29, 150.49, 162.12, $^{31}$P NMR, δ -13.71 (s); HRMS calcd. for C$_{38}$H$_{27}$N$_2$OP (M+1): 559.1939; found: 559.1904.

S-(+)-2-(6-methyl-2-pyridinylcarboxamido)-2'-(diphenylphosphino)-1,1'-binaphthyl (1b):

660 mg of 11 (1.46 mmol) was made according to the same reaction procedure as described for the preparation of 1a. The crude product was loaded on a silica gel column (80 g) and eluted with hexanes: CH$_2$Cl$_2$ (1:2) to afford 747 mg (90%) of 1b as a white solid. mp: 208–209 ° C.,[α]$_D^{25}$+42.0 (c=1.0, CHCl$_3$), $^1$H NMR (CD$_2$Cl$_2$) _1.98 (s, 3H), 6.82–6.87 (m, 2H), 6.99–7.30 (m, 13H), 7.30–7.40 (m, 1H), 7.48–7.57 (m, 2H), 7.64 (t, J=7.7 Hz, 1H), 7.81 (d, J=7.7 Hz, 1H), 7.90–7.98 (m, 2H), 8.06 (t, J=8.2 Hz, 2H), 8.95 (d, J=9.0 Hz, 1H), 9.93 (s, 1H), $^{13}$C NMR, δ 24.06, 119.40, 119.43, 124.36, 124.47, 125.21, 126.42, 126.72, 126.75, 127.10, 127.83, 128.01, 128.60, 128.70, 128.92, 128.95, 129.02, 129.03, 129.06, 129.74, 129.98, 131.08, 131.27, 131.29, 133.58, 133.67, 133.96, 134.00, 134.20, 134.26, 134.47, 135.00, 135.85, 135.88, 137.29, 137.46, 137.90, 138.07, 138.28, 138.52, 138.69, 140.65, 141.10, 149.58, 157.35, 161.95, $^{31}$P NMR, δ -13.77 (s), HRMS calcd for C$_{39}$H$_{29}$N$_2$OP (M+1): 573.2096; found: 573.2051.

3. Preparation of P,N-Schiff-Base Ligand 12:

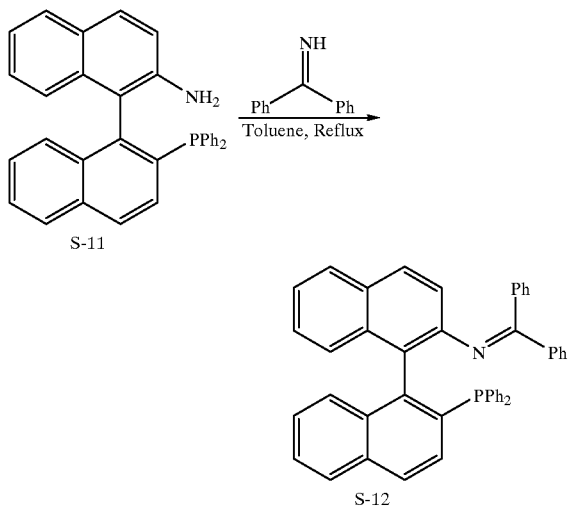

P,N-Schiff-Base Ligand (12):

In a 50 mL of Schlenk flask, 200 mg of S-11 (0.44 mmol) and excess of benzhydrylideneamine (imine) were dissolved in 20 mL of toluene. The solution was refluxed for 12 h. Toluene was removed under reduced pressure, the residue was chromatographed with a hexanes:EtOAc (100:1) mixture to afford 83 mg of pure 12. $^1$H NMR (CDCl$_3$) δ 6.92–6.96 (m, 2H), 7.05–7.09 (m, 2H), 7.17–7.41 (m, 20H), 7.49–7.53 (m, 1H), 7.54 (d, J=8.8 Hz, 1H), 7.57 (dd, J$_1$=8.5 Hz, J$_2$=2.8 Hz, 1H), 7.82 (d, J=8.1 Hz, 1H), 7.87–7.92 (m, 2H), $^{13}$C NMR δ 121.36, 124.31, 125.76, 125.94, 126.06, 126.40, 127.31, 127.33, 127.45, 127.62, 127.69, 127.73, 127.78, 127.93, 128.01, 128.04, 128.10, 128.17, 128.23, 128.46, 128.51, 128.55, 128.99, 129.38, 130.01, 130.13, 130.31, 130.45, 130.46, 132.37, 132.67, 132.76, 132.89, 133.08, 133.65, 133.69, 133.88, 133.91, 133.93, 135.22, 135.33, 136.44, 138.02, 138.17, 138.47, 138.62, 139.47, 143.78, 144.18, 145.93, 166.15, $^{31}$P NMR δ -12.50 (s)

4. Preparation of P,P-Ligand 13:

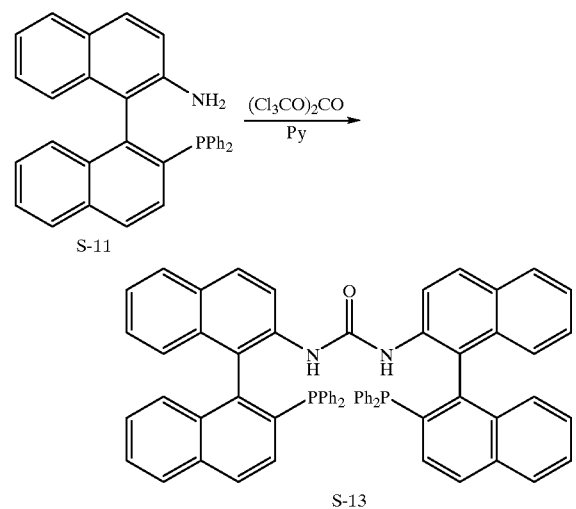

To a mixture of 600 mg of 11 (1.32 mmol) and 80 mg of triphosgene (0.27 mmol), was added 20 mL of dichloromethane under N$_2$ and 5 mL of dried pyridine. The mixture was stirred at room temperature for 8 h. The solvent and pyridine were removed under reduced pressure, the residue was dissolved in 50 mL of dichloromethane and washed with 10 mL of saturated NH$_4$Cl solution and 10 mL of saturated NaHCO$_3$ solution. The organic layer was dried over anhydrous Na$_2$SO$_4$ and concentrated, the residue was chromatographed with CH$_2$Cl$_2$:hexanes (1:1) to recover 200 mg of starting material 11 and then eluted with CH$_2$Cl$_2$:Et$_3$N (10:1) to afford 130 mg of product 13. $^1$H NMR (CD$_2$Cl$_2$) δ 5.70 (s, 2H), 6.68 (d, J=8.5 Hz, 2H), 6.90–7.20 (m, 28H), 7.29 (t, J=7.5 Hz, 2H), 7.41–7.46 (m, 4H), 7.59 (d, J=8.8 Hz, 2H), 7.77 (d, J=8.1 Hz, 2H), 7.97 (d, J=8.2 Hz, 2H), 7.98 (d, J=8.5 Hz, 2H), $^{13}$C NMR δ 122.15, 125.45, 126.28, 126.48, 126.92, 127.07, 127.78, 127.99, 128.60, 128.85, 128.93, 129.03, 129.27, 129.33, 129.59, 129.83, 131.22, 133.28, 134.03, 134.10, 134.27, 134.33, 134.50, 134.73, 137.42, 137.56, 137.71, 137.86, 140.92, 141.30, 152.46, $^{31}$P NMR δ -14.87 (s). FAB-MS m/z 932.8 M$^+$.

Asymmetric Conjugate Addition:

Conjugate addition of various organometallic reagents to enones is one of the most widely used synthetic methods for carbon-carbon bond formation. Many chiral auxiliaries or stoichiometric reagents have been reported for highly stereoselective 1,4-additions. Recently, great attention has been devoted to developing enantioselective catalytic 1,4-addition reactions (N, Krause, *Angew. Chem. Int. Ed. Engl.* 1998, 37, 283). Most notable among these reagents are the chiral phosphorus/Cu(I) complexes, which have proven effective for enantioselective conjugate additions to cyclic enones (e.g., B. L. Feringa, M. Pineschi, L. A. Arnold, R. Imbos, A. H. M. de Vries, *Angew. Chem. Int. Ed. Engl.* 1997, 36, 2620). Despite these advances, highly enantioselective Cu-catalyzed conjugate addition to acyclic enones has not been realized and thus remains as a major synthetic challenge in this area. Because strong substrates dependence is quite common for transition metal-catalyzed asymmetric carbon-carbon bond forming reactions, development of new and enantioselectivity in nonpolar solvents than coordinating solvents such as THF (entries 1–3 vs entry 4). Mixed solvent systems can also be used to achieve good conversion and enantioselectivity (entries 5–7). Removal of the dissociated $CH_3CN$ during the catalyst preparation also helps to increase conversion and enantioselectivity when $Cu(CH_3CN)_4 BF_4$ is used as the catalyst precursor (entry 6 vs entry 5).

TABLE 1

Cu-Catalyzed Enantioselective 1,4-Conjugate Addition of $Et_2Zn$ to 2-Cyclohexen-1-one[a]

| entry | Cu Precursor | solvent | Temp (° C.) | 1a/Cu | Conv. %[b] | ee %[b] |
| --- | --- | --- | --- | --- | --- | --- |
| 1 | $Cu(CH_3CN)_4BF_4$ | toluene | 0 | 2.5 | 82 | 82 |
| 2 | $Cu(CH_3CN)_4BF_4$ | $Cl(CH_2)_2Cl$ | 0 | 2.5 | 58 | 78 |
| 3 | $Cu(CH_3CN)_4BF_4$ | $CH_2Cl_2$ | 0 | 2.5 | 40 | 62 |
| 4 | $Cu(CH_3CN)_4BF_4$ | THF | 0 | 2.5 | 11 | 56 |
| 5 | $Cu(CH_3CN)_4BF_4$ | toluene/$Cl(CH_2)_2Cl$(2:1) | 0 | 2.5 | 76 | 70 |
| 6[c] | $Cu(CH_3CN)_4BF_4$ | toluene/$Cl(CH_2)_2Cl$(2:1) | 0 | 2.5 | 91 | 76 |
| 7[c] | $Cu(CH_3CN)_4BF_4$ | toluene/$Cl(CH_2)_2Cl$(2:1) | −20 | 2.5 | 95 | 85 |
| 8[c] | $Cu(CH_3CN)_4BF_4$ | toluene/$Cl(CH_2)_2Cl$(2:1) | −20 | 1b/Cu = 2.5 | 98 | 92 |
| 9 | $Cu(OTf)_2$ | toluene | 0 | 2.5 | 100 | 72 |
| 10 | $[Cu(OTf)]_2C_6H_6$ | toluene | 0 | 2.5 | 100 | 82 |
| 11 | $[Cu(OTf)]_2C_6H_6$ | toluene | 25 | 2.5 | 100 | 65 |
| 12 | $[Cu(OTf)]_2C_6H_6$ | toluene | −20 | 2.5 | 55 | 87 |
| 13 | $[Cu(OTf)]_2C_6H_6$ | toluene | −40 | 2.5 | 41 | 77 |
| 14 | $[Cu(OTf)]_2C_6H_6$ | toluene | −20 | 1.25 | 72 | 72 |
| 15 | $[Cu(OTf)]_2C_6H_6$ | toluene | −20 | 5.0 | 76 | 91 |
| 16[d] | $[Cu(OTf)]_2C_6H_6$ | toluene | −20 | 2.5 | 100 | 89 |
| 17[d] | $[Cu(OTf)]_2C_6H_6$ | toluene | −20 | 1b/Cu = 2.5 | 100 | 89 |
| 18 | $[Cu(OTf)]_2C_6H_6$ | toluene/$Cl(CH_2)_2Cl$(2:1) | −20 | 1b/Cu = 2.5 | 100 | 87 |

[a]The reaction was carried out at 0° C. for 12 h with 1.0 mmol of the substrate and 1 mol % Cu precursor in 3 mL of solvent.
[b]The conversion were measured by GC analysis and ee's obtained were determined by GC using a chiral Dex column, the absolute configuration was compared with literature.
[c]Removing $CH_3CN$ under vaccum after preparation of the Cu-1a complex.
[d]The reaction was run for 48 h.

chiral ligands plays a pivotal role for overcoming this substrate limitation. Herein we report the synthesis of novel chiral P, N ligands for highly enantioselective Cu-catalyzed conjugate addition of diethylzinc to acyclic enones. In addition, these P, N ligands are also very efficient for Cu-catalyzed conjugate addition of diethylzinc to 2-cyclohexen-1-one.

Two chiral P, N ligands, S-(+)-2-(2-pyridinylcarboxamido)-2'-(diphenylphosphino)-1,1'-binaphthyl (1a, L1) and S-(+)-2-(6-methyl-2-pyridinylcarboxamido)-2'-(diphenylphosphino)-1,1'-binaphthyl (1b, L2) are prepared in high yields from the previously reported compound 11 (S. Vyskocil, M. Smrcina, V. Hanus, M. Polasek, P. Kocovsky, *J. Org. Chem.* 1998, 63, 7738).

We selected 2-cyclohexen-1-one as a typical substrate to develop optimal reaction conditions. The results are summarized in Table 1. The enantioselective 1,4-addition of diethylzinc to 2-cyclohexen-1-one gives better conversion By lowering the reaction temperature from 0° C. to −20° C., 85% ee could be obtained when 1a was used as the chiral P, N ligand (entry 7). Since removing $CH_3CN$ is needed with $Cu(CH_3CN)_4BF_4$ as the catalyst precursor, we chose to use Cu complexes with noncoordinating ligands such as $Cu(OTf)_2$ and $[Cu(OTf)]_2.C_6H_6$ (entries 9 and 10). Our results show that $[Cu(OTf)]_2.C_6H_6$ is an excellent precursor which leads to complete conversion to the 1,4-conjugate addition product with high enantioselectivity (entry 10). The conjugate addition can also be carried out at room temperature, albeit with a lower enantioselectivity (entry 11). The optimal reaction temperature for obtaining high enantioselectivity is −20° C. (entries 12 and 13). The enantioselectivity with the ratio of 1a/Cu=2.5 is significantly higher than the result obtained with the ratio of 1a/Cu=1.25 (entry 12 vs 14). Addition of ligand beyond two equivalents has only a marginal effect on enantioselectivity (entry 12 vs 15). Finally, replacing 1a with a sterically more hindered chiral P, N ligand 1b gives comparable or better results for enantioselective 1,4-conjugate addition to 2-cyclohexen-1-one (entries 7 and 8, entries 16 and 17). Our experiments indicate that [Cu(OTf)]$_2$.C$_6$H$_6$ is a preferred copper catalyst precursor and nonpolar solvents such as toluene or Cl(CH$_2$)$_2$Cl are desirable.

An effective catalytic systems for a variety of acyclic enones is shown in Table 2.

TABLE 2

Cu-Catalyzed Enantioselective 1,4-Conjugate Addition[a]

R$_1$—CH=CH—C(=O)—R$_2$ + Et$_2$Zn $\xrightarrow{\text{[Cu(OTf)]}_2\text{C}_6\text{H}_6/\text{1a or 1b}}_{\text{solvent, -20° C., 48 h}}$ R$_1$—CH(Et)—CH$_2$—C(=O)—R$_2$

| entry | R$_1$ | R$_2$ | ligand | Solvent | yield % | ee %[b] | conf[c] |
|---|---|---|---|---|---|---|---|
| 1 | Ph | Ph | 1a | toluene/Cl(CH$_2$)$_2$Cl(2:1) | 92 | 83 | S |
| 2 | Ph | Ph | 1b | toluene/Cl(CH$_2$)$_2$Cl(2:1) | 85 | 96 | S |
| 3 | Ph | Ph | 1b | toluene | 72 | 94 | S |
| 4 | Ph | 4-CH$_3$O—C$_6$H$_4$ | 1b | toluene/Cl(CH$_2$)$_2$Cl(2:1) | 69 | 97 | —[d] |
| 5 | Ph | 4-CH$_3$O—C$_6$H$_4$ | 1b | toluene | 10 | 90 | —[d] |
| 6 | 4-CH$_3$O—C$_6$H$_4$ | Ph | 1b | toluene/Cl(CH$_2$)$_2$Cl(2:1) | 97 | 98 | S |
| 7 | 4-Cl—C$_6$H$_4$ | Ph | 1b | toluene/Cl(CH$_2$)$_2$Cl(2:1) | 72 | 95 | +[d] |
| 8 | Ph | 4-Cl—C$_6$H$_4$ | 1b | toluene/Cl(CH$_2$)$_2$Cl(2:1) | 70 | 95 | —[d] |
| 9 | Ph | CH$_3$ | 1b | toluene/Cl(CH$_2$)$_2$Cl(2:1) | 70 | 90 | S |
| 10 | i-Pr | CH$_3$ | 1b | toluene | 53 | 86 | +[d] |

[a]The reaction was carried out at -20° C. for 48 h in 1 mL of toluene and 0.5 mL of ClCH$_2$CH$_2$Cl [substrate (0.5 mmol)/[Cu(OTf)]$_2$C$_6$H$_6$/ligand = 1:0.01:0.05], or in 1.5 mL of toluene.
[b]The ee's were determined by chiral HPLC.
[c]The absolute configuration was assigned by comparison of optical rotation with reported data. [3,4]
[d]Sign of the optical rotation.

Chalcone is chosen as the substrate for testing reaction conditions. The experimental results show that enantioselective conjugate addition of diethylzinc to chalcone catalyzed by a Cu(I)-1b species (entry 2) gives better ee than that obtained with a Cu(I)-1a compound (entry 1). Reaction in the mixed solvent system (toluene/Cl(CH$_2$)$_2$Cl) appears to be even better than that carried out in toluene both in terms of conversion and enantioselectivity (entry 2 vs entry 3). A possible explanation for this result that substrates are more soluble in the mixed solvent system. This is especially true for a methoxy-substituted chalcone (entry 4 vs entry 5). Under the optimal conditions for enantioselective 1,4-addition of diethylzinc to chalcone (entry 2), several acyclic enones with aryl substituent groups have been successfully converted to the corresponding chiral ketones (entries 4–9, up to 98%ee). To our knowledge, the enantioselectivities achieved in this study are the best yet reported for the Cu-catalyzed enantioselective conjugate addition to acyclic enones. Furthermore, a very promising result has been obtained for an acyclic enone with only aliphatic substituents (entry 10, 86%ee).

General Procedure for Asymmetric 1,4-Conjugate Addition:

In a N$_2$-filled glovebox, 10.0 mg of [Cu(OTf)]$_2$.C$_6$H$_6$ (2 mmol) and 57.2 mg of 1b (10 mmol) with 4 mL of 1,2-dichloroethane and 8 mL of toluene were added to a Schlenk tube. This solution was stirred at room temperature for 0.5 hr. This catalyst solution was used for four separate experiments. To a dried Schlenk tube was added 0.5 mmol of enone and then 3 mL of the catalyst solution. The solution was stirred at room temperature for 10 min and then cooled to -20° C. After the solution was stirred at -20° C. for 15 min, 0.75 mL of Et$_2$Zn (1.0 M in hexanes, 0.75 mmol) was added slowly. The resulting mixture was stirred at -20° C. for 48 h and 2 mL of 5% of dilute hydrochloric acid was added. After warming to room temperature, 10 mL of Et$_2$O was added. The organic phase was washed with 5 mL of saturated NaHCO$_3$, dried over anhydrous Na$_2$SO$_4$ and concentrated under vacuum. The residue was loaded on a silica gel column and eluted with EtOAc:hexanes (1:20–40) to afford the addition product. All chiral 1,4-addition products are known compounds.

Determination of Enantiomeric Excesses:

a) Chiral Capillary GC Column:

Supelco™ γ-DEX 225 (30 m×0.25 mm (i.d.)). Racemic products were obtained by 1,4-addition of substrates with ethyl magnesium bromide (1.0 M in THF) in THF at room temperature. The following is the retention time for the racemic products: 3-ethylcyclohexanone, temp=80° C. for 40 min then 120° C., $t_S$=42.93 min, $t_R$=43.27 min; 4-ethyl-5-methyl-hexan-2-one, temperature=80° C., $t_1$=23.25 min, $t_S$=23.92 min; and 4-phenyl-hexan-2-one, temp=120° C., $t_S$=32.25 min, $t_R$=33.32 min. b) Chiral HPLC Columns: Daicel Chiralcel OD and Chiralpak AD, particle size: 5.0 μm, column dimensions: 25 cm (length)×0.46 cm (i.d.), flow=1.0 mL/min. 1,3-diphenyl-pentan-1-one. (Chiralpak AD, 2-PrOH/hexanes=1:99), $t_S$=20.43 min, $t_R$=29.55 min; 3-(4-methoxyphenyl)-1-phenyl-pentan-1-one (Chiralpak AD, 2-PrOH/hexanes=10:90), $t_1$=12.65 min, $t_2$=16.83 min; 1-(4-methoxyphenyl)-3-phenyl-pentan-1-one (Chiralcel OD, 2-PrOH/hexanes=10:90), $t_S$=19.80 min, $t_R$=22.37 min; 3-(4-chlorophenyl)-1-phenyl-pentan-1-one (Chiralpak AD, 2-PrOH/hexanes=5:95), $t_1$=10.73 min, $t_2$=13.87 min; and 1-(3-chlorophenyl)-4-phenyl-pentan-1-one. (Chiralpak AD, 2-PrOH/hexanes=1:99), $t_1$=25.73 min, $t_2$=34.97 min.

III. Tridentate Ligand Synthesis

1. Preparation of Schiff-Base Ligand 14, 15, and 16:

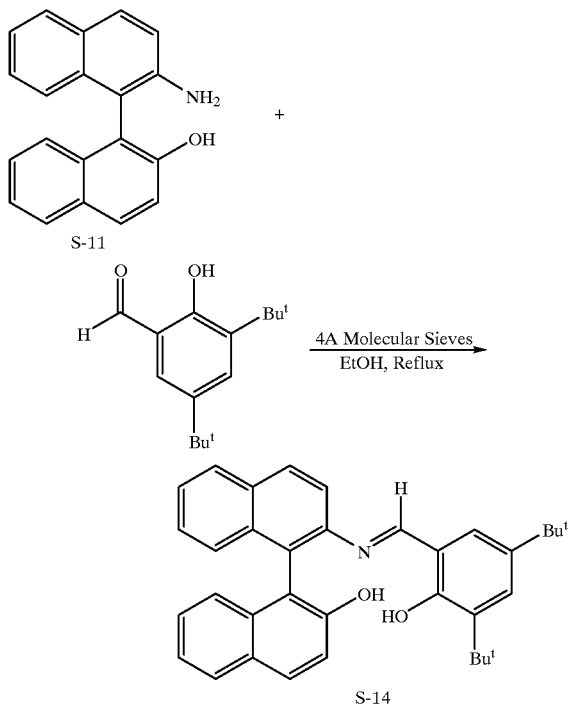

Tridentate Schiff-Base Ligand 14:

To a mixture of 670 mg of S-6 (2.35 mmol) 562 mg of 3,5-di-tert-butyl-2-hydroxybenzaldehyde (Lancaster) (2.40 mmol) and 1.0 g of 4 Å molecular sieves, 25 mL of absolute EtOH was added under $N_2$. The mixture was refluxed for 24 h. The molecular sieves were filtered off and the filtrate was concentrated to obtain a yellow oily liquid. The product was purified by silica gel (60 g) column, which was pretreated with 100 mL of hexanes:triethylamine (10:1), eluted with hexanes:EtOAc (4:1) to collect an orange belt. The orange solution was concentrated to afford 1.03 g (87%) of pure 14. $^1$H NMR ($CD_2Cl_2$) □δ 1.21 (s, 9H), 1.26 (s, 9H), 7.01 (d, J=8.3 Hz, 1H), 7.12 (d, J=2.4 Hz, 1H), 7.19–7.23 (m, 1H), 7.28–7.34 (m, 3H), 7.37–7.39 (m, 2H), 7.50–7.54 (m, 1H), 7.70 (d, J=8.8 Hz, 1H), 7.87 (d, J=8.0 Hz, 1H), 7.94 (d, J=8.9 Hz, 1H), 8.02 (d, J=8.2 Hz, 1H), 8.16 (d, J=8.8 Hz, 1H), 8.71 (s, 1H), 12.60 (s, 1H), $^{13}$C NMR δ 29.4, 31.6, 34.4, 35.2, 116.7, 118.1, 118.4, 118.6, 123.4, 124.8, 126.4, 126.5, 126.7, 126.8, 127.2, 127.6, 128.4, 128.5, 128.7, 129.5, 130.3, 130.8, 133.1, 134.1, 134.2, 137.1, 140.7, 145.5, 152.3, 158.6, 163.7; FAB-MS m/z 502.4 (M+1)$^+$.

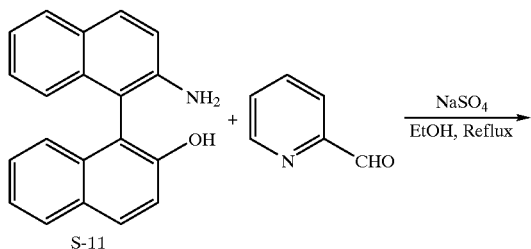

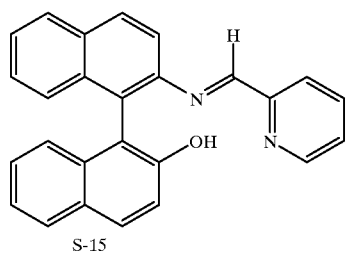

Tridentate Schiff-Base Ligand 15:

To a mixture of 352 mg of S-6 (1.24 mmol), 300 mg of 2-pyridine carboxylic aldehyde (2.40 mmol) and 1.09 g of anhydrous $Na_2SO_4$, was added 30 mL of absolute EtOH. The mixture was refluxed for 30 h, and filtered. The filtrate was concentrated and the residue was treated with 30 mL of diethyl ether:hexanes (1:5) to afford 340 mg of yellow solid (74%). $^1$H NMR ($CD_3COCD_3$) δ, 7.03 (d, J=8.2 Hz, 1H), 7.15–7.25 (m, 6H), 7.43–7.48 (m, 1H), 7.54–7.58 (m, 2H), 7.61–7.65 (m, 1H), 7.83–7.89 (m, 2H), 8.10 (d, J=8.7 Hz, 2H), 8.55–8.57 (m, 2H), $^{13}$C NMR δ 117.8, 119.5, 120.7, 121.9, 123.9, 126.0, 126.1, 126.3, 126.4, 127.3, 127.4, 127.8, 129.2, 129.4, 129.9, 130.6, 130.7, 133.8, 135.1, 135.4, 137.6, 149.9, 150.7, 154.2, 156.1, 162.6.

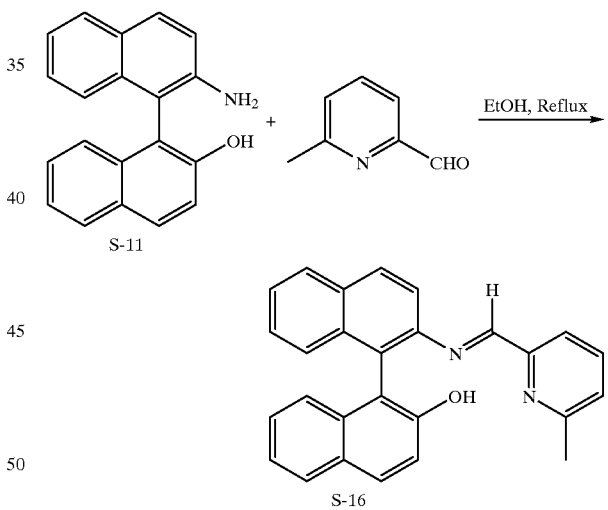

Tridentate Schiff-Base Ligand 16:

To a mixture of 286 mg of S-6 (1.00 mmol), 215 mg of 6-methyl-2-pyridine carboxylic aldehyde (1.55 mmol), was added 10 mL of absolute EtOH. The mixture was refluxed 24 h, filtered. The yellow solid was washed with 10 mL of ether and dried to obtain 288 mg of yellow solid (74%). $^1$H NMR ($CD_3COCD_3$) δ, 2.46 (s, 3H), 7.02 (d, J=8.2 Hz, 1H), 7.17–7.36 (m, 7H), 7.41–7.55 (m, 3H), 7.82–7.88 (m, 2H), 8.01 (d, J=8.3 Hz, 1H), 8.09 (d, J=8.7 Hz, 1H), 8.50 (s, 1H), FAB-MS m/z 389.1 (M+1)$^+$.

2. Preparation of C$_2$-Symmetry Tridentate Ligand 17:

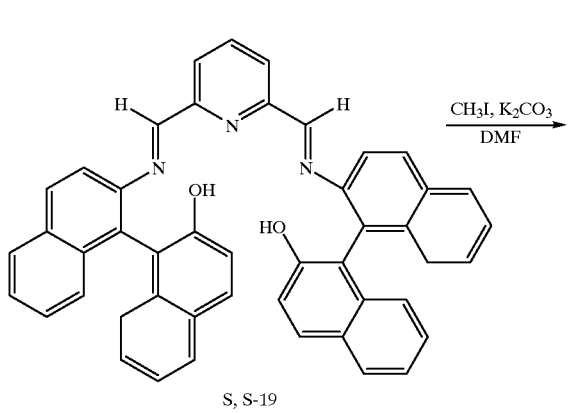

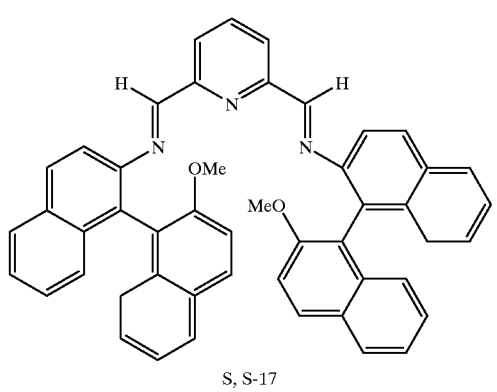

C$_2$-Symmetry Tridentate Ligand S,S-17:

To a mixture of 338 mg of crude pentadentate ligand S,S-19 (according to $^1$H NMR, 95% pure), 280 mg of K$_2$CO$_3$ and 8 mL of dried DMF, was added 200 µL of CH$_3$I. The mixture was stirred at room temperature for 8 h. DMF was pumped down, the residue was treated with 20 mL of dichloromethane and filtered. The filtrate was concentrated in vacuo. The residue was dissolved in 5 mL of acetone and then poured into 50 mL of hexanes. The precipitate was collected and dried to afford 185 mg of yellow solid (53%). $^1$H NMR (CD$_3$COCD$_3$) δ 3.70 (s, 6H), 7.03 (d, J=8.3 Hz, 2H), 7.15–7.31 (m, 9H), 7.41–7.52 (m, 8H), 7.56 (d, J=8.8 Hz, 2H), 7.88 (d, J=7.9 Hz, 2H), 7.99–8.02 (m, 5H), 8.10 (d, J=8.7 Hz, 2H), 8.47 (s, 2H).

IV. Tetradentate Ligand Synthesis

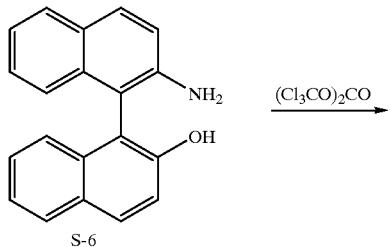

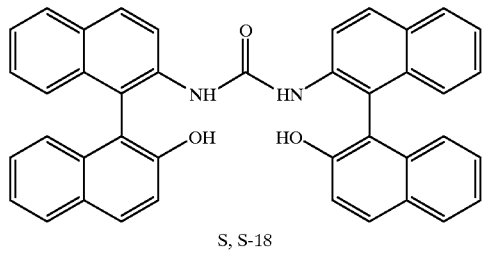

Tetradentate Ligand S,S-18:

To a solution of 583 mg of S-6 (2.05 mmol) in 10 mL of pyridine, was added 100mg of triphosgene (0.337 mmol). The solution turned red instantly. The mixture was stirred at room temperature for 4 h, the refluxed overnight. TLC showed the presence of S-6, so 80 mg of triphosgene (0.27 mmol) was added, and the above procedure was repeated. Pyridine was removed under reduced pressure, the residue was dissolved in CH$_2$Cl$_2$, separated using silica gel (50 g) column and eluted with hexanes:EtOAc (4:1) to recover 50 mg of S-6, while eluted with hexanes:EtoAc (1:1) to afford 480 mg of S,S-18 (86%). $^1$H NMR (CDCl$_3$) δ 6.19 (s, 2H), 6.78 (d, J=8.5 Hz, 2H), 7.04–7.08 (m, 4H), 7.14–7.19 (m, 2H), 7.21–7.26 (m, 2H), 7.28–7.33 (m, 2H), 7.39–7.44 (m, 2H), 7.69 (t, J=8.8 Hz, 4H), 7.78–7.85 (m, 6H), $^{13}$C NMR δ 113.8, 118.2, 121.7, 122.0, 124.0, 124.4, 125.8, 126.0, 127.4, 128.6, 128.7, 129.4, 130.4, 131.1, 131.5, 133.3, 133.5, 134.8, 152.2, 154.6.

V. Pentadentate Ligand synthesis:

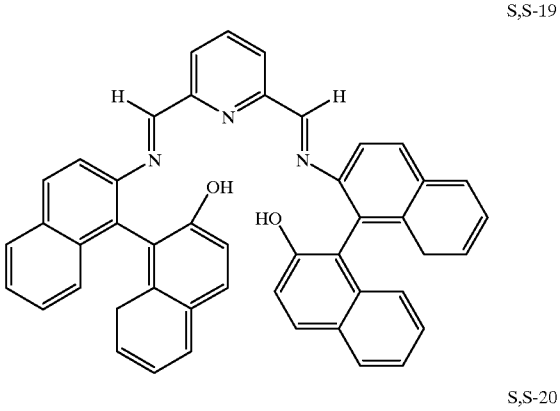

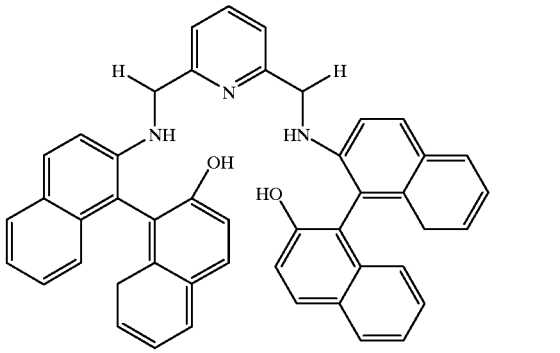

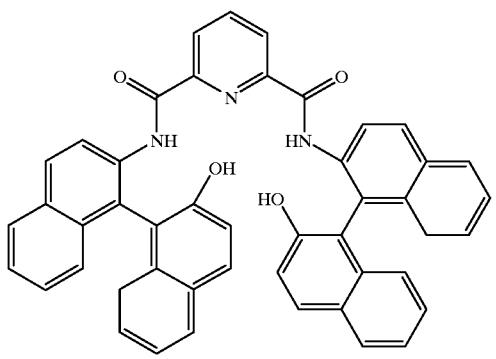

S,S-21

Preparation of 2,6-Pyridinedicarboxaldehyde:

This preparation procedure followed the literature procedure (J. Chem. Soc., Dalton Trans. 1984–1937). To the mixture of 11.51 g of 2,6-pyridine-dimethanol (8.28 mmol) and 9.99 g of $SeO_2$, was added 200 mL of 1,4-dioxane. The mixture was then refluxed for 4 h and filtered. The filtrate was concentrated under reduced pressure. The solid was dissolved in $CH_2Cl_2$ and passed through a silica gel plug. The solution was concentrated, and the solid was recrystallized from 60 mL of acetone and 100 mL of hexanes to afford 9.6 g of white crystal (71%), which was kept under $N_2$. $^1$H NMR ($CDCl_3$) δ 8.02–8.12 (m, 3H), 10.08 (s, 2H), $^{13}$C NMR δ 125.7, 138.8, 153.3, 192.7.

Racemic Pentadentate Ligand 19:

In a round bottom flask, which was equipped with Soxhlet Extractor containing 4 Å molecular sieves for removing water, were added 1.20 g of 2,6-pyridine dicarboxaldehyde (8.89 mmol) and 6.03 g of racemic NOBIN 5 (2.12 mmol) and 100 mL of absolute EtOH. The mixture was refluxed for 24 h. The solvent was concentrated under reduced pressure. The residue solid was transferred into Soxhlet extraction thimble, the impurities were extracted by $Et_2O$ for 10 h. The residue in thimble was dried to obtain 3.65 g of pale yellow solid (61%). $^1$H NMR ($CD_3COCD_3$) δ 7.00 (d, J=8.4 Hz, 2H), 7.16–7.30 (m, 10H), 7.40–7.50 (m, 4H), 7.56 (d, J=8,7 Hz, 2H), 7.80–7.86 (m, 4H), 7.99–8.02 (m, 3H), 9.09 (d, J=8.7 Hz, 2H), 8.54 (s, 2H), $^{13}$C NMR δ 117.78, 119.44, 120.52, 123.22, 123.94, 126.08, 126.31, 126.54, 127.35, 127.42, 127.81, 129.24, 129.46, 129.89, 130.65, 130.76, 133.84, 135.07, 135.38, 138.28, 149.63, 154.21, 155.92, 161.83.

Ligand S,S-19:

Using the same procedure did not produce pure ligand by $^1$H NMR. The product contained some half Schiff-Base half aldehyde. The best ratio was 20:1 by $^1$H NMR.

Pentadentate Ligand S,S-20:

To a solution of 1 g of above S,S-19 in 20 mL of 95% EtOH, was added 1.0 g of $NaBH_4$ in three portions. The mixture was stirred at room temperature for 4 h, then filtered, and the filtrate was concentrated. The residue was dissolved in 50 mL of $CH_2Cl_2$ and washed with 10 mL of $NH_4Cl$ and 10 mL of saturated $NaHCO_3$, dried over anhydrous $Na_2SO_4$. The solvent was concentrated, the residue was loaded on silica gel (60 g) column and eluted with $Et_3N:CH_2Cl_2$:hexanes mixture (1:5:2) to afford 600 mg of product as a white solid. $^1$H NMR ($CD_3COCD_3$) δ 4.30–4.44 (m, 4H), 6.87–6.90 (m, 2H), 7.01 (d, J=9.0 Hz, 2H), 7.05 (d, J=8.3 Hz, 2H), 7.08–7.29 (m, 11H), 7.39 (d, J=8.9 Hz, 2H), 7.48 (t, J=7.7 Hz, 1H), 7.70–7.61 (m, 4H), 7.88 (d, J=7.9 Hz, 2H), 7.93–7.96 (m, 3H), $^{13}$C NMR δ 49.5, 112.5, 115.6, 116.1, 120.2, 120.6, 122.6, 124.3, 125.0, 125.9, 127.4, 127.6, 128.8, 129.3, 129.5, 130.7, 130.8, 131.1, 135.6, 135.7, 138.2, 146.0, 154.8, 160.1, FAB-MS m/z 674 $(M+1)^+$.

Pentadentate Ligand S,S-21:

In a round bottom flask, were added 849 mg of S-6 (2.98 mmol), 306 mg of freshly distilled (bulb-to-bulb) 2,6-pyridine dicarboxylic acid chloride (1.52 mmol), 2 mL of 2,6-lutidine and 18 ml of dried DMF. The mixture was turned into yellow color quickly, and it was stirred at room temperature overnight. DMF and 2,6-lutidine was removed under reduced pressure. The residue was separated using a silica gel (40 g) plug to obtain a crude product. This crude product contained by-products with almost the same polarity on TLC, which may be diester and one side ester, one side amide compound. So the crude product was dissolved in 100 mL of THF and 20 mL of water contained 2.0 g of $K_2CO_3$. The solution was stirred at room temperature for 12 h. THF was removed under reduced pressure. The organic compound was extracted with 100 mL of EtOAc. The organic phase was washed with 20 mL of saturated $NH_4Cl$ solution, 20 mL of saturated $NaHCO_3$ solution and 20 mL of brine consequently, dried over anhydrous $Na_2SO_4$, and concentrated. The solid was separated by silica gel (100 g) column and eluted with hexanes:EtOAc:$Et_3N$ (10:10:1) to afford 700 mg of S,S-21 (67%) as a white solid. $^1$H NMR (DMSO-$d_6$) δ 6.73 (d, J=8.2 Hz, 2H), 7.04–7.14 (m, 6H), 7.25 (d, J=8.9 Hz, 2H), 7.26–7.36 (m, 2H), 7.50–7.54 (m, 2H), 7.72 (d, J=7.6 Hz, 2H), 7.78 (d, J=8.9 Hz, 2H), 7.87 (d, J=7.6 Hz, 2H), 7.98 (t, J=7.6 Hz, 1H), 8.11 (d, J=8.1 Hz, 2 H), 8.24 (s, 4H), 9.01 (s, 2H), 9.71 (bs, 2H). $^{13}$C NMR δ 113.8, 118.8, 122.9, 123.9, 124.0, 124.9, 125.7, 126.4 (2×C), 126.7, 126.8, 128.2, 128.4 (3×C), 130.4, 131.7, 133.0, 133.5, 134.2, 140.1, 149.2, 153.4, 162.0. FAB-MS m/z 702.68 $(M+1)^+$.

Asymmetric Cyclopropanation:

In a $N_2$-filled glovebox, 10 mg of [Cu(OTf)]$_2$.$C_6H_6$ (0.02 mmol) was added in a Schlenk tube, 2 mL of $CH_2Cl_2$ was added to dissolve the catalyst precursor, then 1.2 eq of chiral ligand to Cu(I) or ligand solution (usually 1.0 M in toluene) was added, and 1 mL of $CH_2Cl_2$ was added to wash solution. The mixture was stirred for 5 min, then 1.04 g of styrene (10.0 mmol) and 3 mL of $CH_2Cl_2$ were added. This mixture was stirred at room temperature for 20 min. Meanwhile, to a 2-drum vial, 0.270 g of $N_2$CHCOOEt (90%, 2.13 mmol) was diluted by 2 mL of $CH_2Cl_2$. This solution was added into the Schlenk tube through a syringe pump during a period of 6 h. Then let it stirred at room temperature for 1 more hour. The reaction sample was passed through a Basic $Al_2O_3$ plug, washed the plug with $Et_2O$. The catalyst-free solution was analyzed by chiral capillary GC (see Table 3).

Determination of Enantiomeric Excesses:

Chiral Capillary GC column: Supelco™ β-dex-120, 30 m×0.25 mm (i.d.). Racemic sample was obtained by the same method catalyzed by Cu(acac)2. The following is the retention time for the cyclopropanation products and by-products-diethyl fumarate and diethyl maleate. Temp= 115° C., $t_{diethyl\ fumarate}$=8.16 min, $t_{diethyl\ maleate}$=9.48 min; $t_1$=44.18 min, $t_2$=45.97 min (two cis isomers); $t_3$=53.00 min, $t_4$=54.24 min (two trans isomers). The ratio of cis isomers to trans isomers:29:71. The ee's of chiral reactions are listed in Table 3.

TABLE 3

Asymmetric cyclopropanation[a]

| Entry | Precursor | ligand | by-product (%) | cis/trans (%) | cis ee (%) | trans ee (%) |
|---|---|---|---|---|---|---|
| 1 | [Cu(OTf)]$_2$·C$_6$H$_6$ | S,S-19 | trace | 42/58 | 8 | 4 |
| 2[b] | [Cu(OTf)]$_2$·C$_6$H$_6$ | S,S-19 | trace | 37/63 | 8 | 8 |
| 3 | [Cu(OTf)]$_2$·C$_6$H$_6$ | S-16 | trace | 31/69 | 34 | 19 |
| 4 | [Cu(OTf)]$_2$·C$_6$H$_6$ | S-15 | 1 | 29/71 | 2 | 4 |
| 5 | [Cu(OTf)]$_2$·C$_6$H$_6$ | S,S-17 | 0.2 | 42/58 | 18 | 6 |
| 6 | [Cu(OTf)]$_2$·C$_6$H$_6$ | S-14 | 0 | 22/78 | / | 5 |
| 7 | [Ru(cymene)Cl$_2$]$_2$ | S,S-19 | 34 | 32/68 | 2 | 5 |
| 8 | [Ru(cymene)Cl$_2$]$_2$ | S,S-17 | 56 | 43/57 | 10 | 2 |

[a]. The reaction condition was described before.
[b]. The mixture of Cu precursor and ligand was stirred for 40 min.

Synthesis of 2-Amino-2'-hydroxy-1,1'-binaphthyl(NOBIN):

To a 125 mL Teflon lined autoclave was added 5 g (17.5 mmol) of 1,1'-bi-2-naphthol, 23.47 g (175 mmol) of (NH$_4$)$_2$SO$_3$H$_2$O and 65 mL of concentrated aqueous ammonia. The mixture was heated in an oil-bath to 200° C. for 5 days, then cooled down to ambient temperature and filtered. The resulting solid was washed with water followed by recrystallization from benzene to afford 4.52 g (15.8 mmol, 91%) of pure 2-amino-2'-hydroxy-1,1'-binaphthyl. Enantiomerically pure NOBIN can be obtained by the resolution methods reported in the literature (Ding, K.; Wang, Y.; Yun, H.; Lin, J.; Wu, Y.; Terada, M.; Okubs, Y.; Mikami, K.; Chem. Eur. J. 1999, 5, 1734–1737).

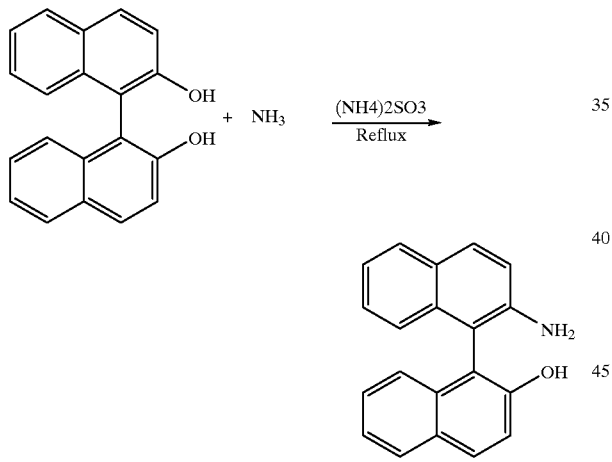

Cyclopropanation with a Ru-L18 Complex

A new chiral ruthenium complex has been designed and synthesized, which has been successfully used in catalyzing asymmetric cyclopropanation reaction. High enantioselectivities (83%–96%) of have been achieved for trans cyclopropanation products.

In the course of seeking new ligands with good chiral environment, an N, O-mixed pentadentate Schiff base ligand (L18) was prepared, which is accessible from chiral 2-amino-2'-hydroxy-1,1'-binaphthyl (NOBIN) and 2,6-pyridinedicarboxaldehyde. This pentadentate ligand was obtained in 75% unoptimized yield with an impurity of <5% mono Schiffbase.6 We therefore attempted to make its Ru complex by refluxing this ligand, [RuIICl2(p-cymene)]2, and pyridine in an isopropanol solution. A dark purple solution resulted, which after column chromatography gave Ru complex in 30% yield). $^1$H and $^{13}$C NMR spectra showed complex the Ru compound had a C2-symmetrical structure. Molecular simulation suggests that the Ru-complex had an octahedral Ru metal center, which was coordinated with four N atoms and two O atoms. The two O atoms located at trans position of the Ru metal center.

Different pyridine derivatives were also used to make Ru complexes. It was found that the preparation method used for generating Ru compound were generally applicable for different pyridine derivatives such as 2-picoline, 2,6-lutidine, and halopyridines. However, purification turned out to be elusive to most of those complexes due to their high sensitivity to oxygen. We finally found a new Ru complex which could be synthesized in a pure form from the pentadentate ligand, [RuIICl2(p-cymene)]2, and 2-chloropyridine in 57% yield, showed high reactivity towards EDA at room temperature. The new Ru complex was used for catalytic asymmetric cyclopropanation of styrene and ethyl diazoacetate. It was found that in the presence of 1 mol % of the new Ru complex, the cyclopropanation reaction could proceed smoothly to afford 2-phenylcyclopropanecarboxylates and with high trans-cis selectivity (90:10) and high enantioselectivity (up to 97% ee), while more catalyst loading did not improve the reaction yield and ee's of the products.

Alternative work-up and isolation procedures are also possible, and will be evident to those skilled in the art.

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

What is claimed is:

1. A ligand selected from the group consisting of compounds represented by C through E;

wherein C is represented by the formula selected from the group consisting of:

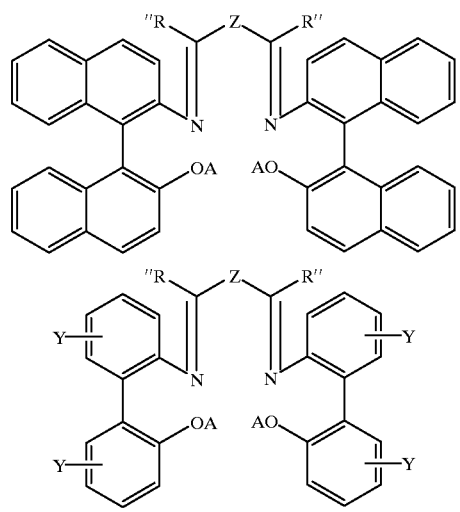

wherein each Y is independently selected from the group consisting of: H, one or more halide, alkyl, aryl, alkoxide, nitro and carboxylate; each R" is independently selected from the group consisting of: H, alkyl, substituted alkyl, aryl, substituted aryl, 1,2-, 1,3- or 1,4-arylene, and a group that is part of an aryl system; Z is selected from the group consisting of: $(CH_2)_n$ wherein n is 0, 1 or 2, $CR_2$ wherein R is alkyl or aryl, aryl, substituted aryl, heteroaryl, phenol and aryl carboxylate; and each A is independently selected from the group consisting of: H, alkyl and substituted alkyl;

wherein D is represented by the formula selected from the group consisting of:

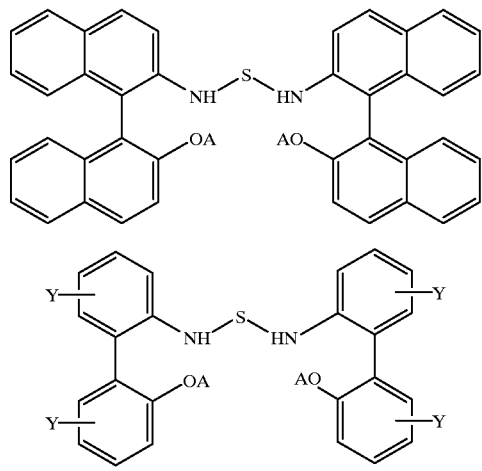

wherein each Y is independently selected from the group consisting of: H, one or more halide, alkyl, aryl, alkoxide, nitro and carboxylate; each R" is independently selected from the group consisting of: H, alkyl, substituted alkyl, aryl, substituted aryl, and a group that is part of an aryl system; S is independently selected from the group consisting of: $(CH_2)_n$ wherein n is 2–6 and $CH_2(Ar)CH_2$ wherein Ar is arylene or substituted arylene; and each A is independently selected from the group consisting of: H, alkyl and substituted alkyl; and wherein E is represented by the formula selected from the group consisting of:

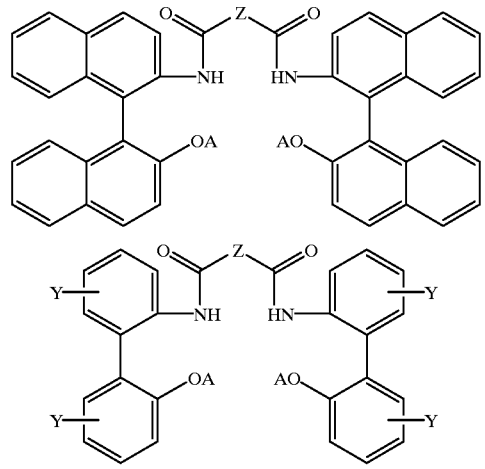

-continued

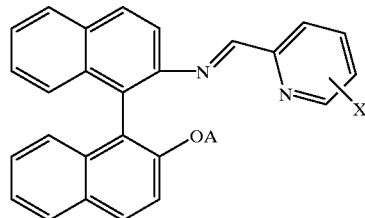

wherein each X and Y is independently selected from the group consisting of: H, one or more halide, alkyl, aryl, alkoxide, nitro and carboxylate; Z is selected from the group consisting of: $(CH_2)_n$ wherein n is 0, 1 or 2, $CR_2$ wherein R is alkyl or aryl, aryl, 1,2-, 1,3- or 1,4-arylene, substituted aryl, heteroaryl, phenol and aryl carboxylate; and each A is independently selected from the group consisting of: H, alkyl and substituted alkyl.

2. The ligand of claim 1, wherein each of said heteroaryl groups is independently selected from the group consisting of: a nitrogen heteroaryl, a sulfur heteroaryl and an oxygen heteroaryl.

3. The ligand of claim 1, wherein said ligand is one of the enantiomers.

4. The ligand of claim 1, wherein said ligand is a racemic mixture of enantiomers.

5. The ligand of claim 1, wherein said ligand is a non-racemic mixture of enantiomers.

6. The ligand of claim 1, having an optical purity of at least 85% ee.

7. A catalyst prepared by a process comprising: contacting a transition metal salt, or a complex thereof, and a ligand selected from the group consisting of compounds represented by C through E;

wherein C is represented by the formula selected from the group consisting of:

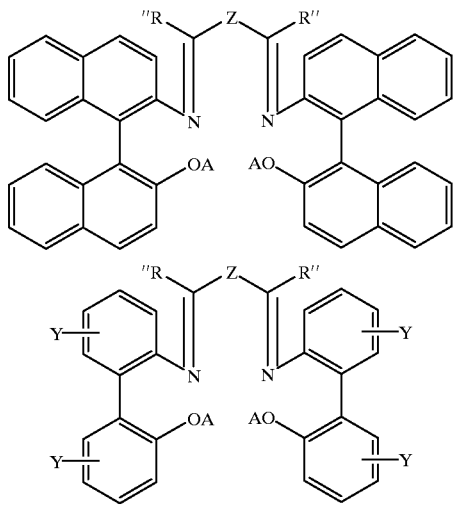

wherein each Y is independently selected from the group consisting of: H, one or more halide, alkyl, aryl, alkoxide, nitro and carboxylate; each R" is independently selected from the group consisting of: H, alkyl, substituted alkyl, aryl, substituted aryl, 1,2-, 1,3- or 1,4-arylene, and a group that is part of an aryl system; Z is selected from the group consisting of: $(CH_2)_n$ wherein n is 0, 1 or 2, $CR_2$ wherein R is alkyl or aryl, aryl, substituted aryl, heteroaryl, phenol and aryl carboxylate; and each A is independently selected from the group consisting of: H, alkyl and substituted alkyl;

wherein D is represented by the formula selected from the group consisting of:

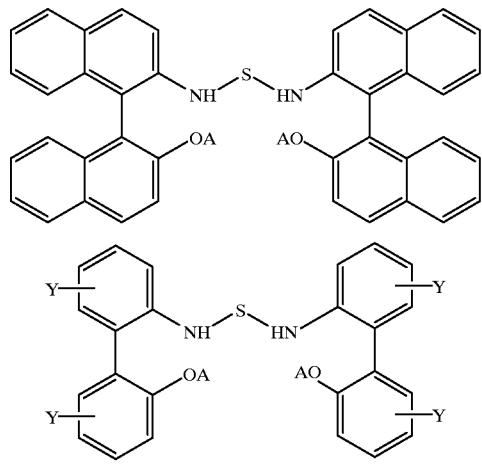

wherein each Y is independently selected from the group consisting of: H, one or more halide, alkyl, aryl, alkoxide, nitro and carboxylate; each R" is independently selected from the group consisting of: H, alkyl, substituted alkyl, aryl, substituted aryl, and a group that is part of an aryl system; S is independently selected from the group consisting of: $(CH_2)_n$ wherein n is 2–6 and $CH_2(Ar)CH_2$ wherein Ar is arylene or substituted arylene; and each A is independently selected from the group consisting of: H, alkyl and substituted alkyl; and wherein E is represented by the formula selected from the group consisting of:

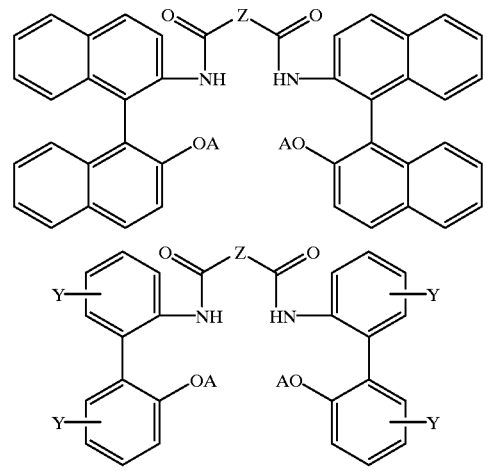

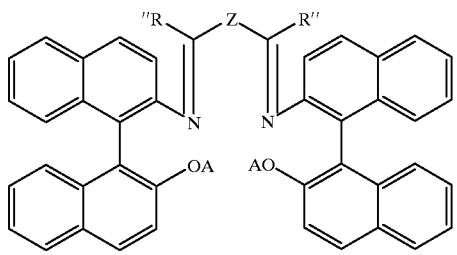

wherein each X and Y is independently selected from the group consisting of: H, one or more halide, alkyl, aryl, alkoxide, nitro and carboxylate; Z is selected from the group consisting of: $(CH_2)_n$ wherein n is 0, 1 or 2, $CR_2$ wherein R is alkyl or aryl, aryl, 1,2-, 1,3- or 1,4-arylene, substituted aryl, heteroaryl, phenol and aryl carboxylate; and each A is independently selected from the group consisting of: H, alkyl and substituted alkyl.

8. The catalyst of claim 7, having an optical purity of at least 85% ee.

9. The catalyst of claim 8, wherein said transition metal is selected from the group consisting of: Pd, Rh, Ru, Ir, Cu, Ni, Mo, Ti, V, Re and Mn.

10. The catalyst of claim 9, wherein said transition metal salt, or complex thereof, is selected from the group consisting of: $Pd_2(DBA)_3$; $Pd(OAc)_2$; $[Rh(COD)Cl]_2$; $[Rh(COD)_2]X$; $Rh(acac)(CO)_2$; $RuCl_2(COD)$; $RuCl_2(=CHR)(PR'_3)_2$; $Ru(COD)(methylallyl)_2$; $Ru(ArH)Cl_2$; $[Ir(COD)_2Cl]_2$; $[Ir(COD)_2]X$; $Cu(OTf)$; $Cu(OTf)_2$; $Cu(Ar)X$; $CuX$; $NiX_2$; $MoO_2(acac)_2$; $Ti(OiPr)_4$; $VO(acac)_2$; $MeReO_3$; $MnX_2$ and $Mn(acac)_2$; wherein each R and R' is independently selected from the group consisting of: alkyl or aryl; Ar is an aryl group; and X is a counteranion.

11. The catalyst of claim 10, prepared in situ or as an isolated compound.

12. A process for preparation of an asymmetric compound comprising: contacting a substrate capable of forming an asymmetric product by an asymmetric reaction and a catalyst prepared by a process comprising: contacting a transition metal salt, or a complex thereof, and a ligand selected from the group consisting of compounds represented by C through E;

wherein C is represented by the formula selected from the group consisting of:

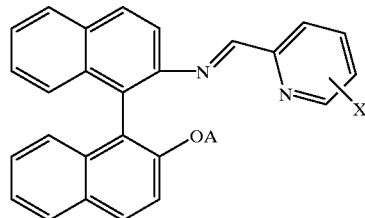

-continued

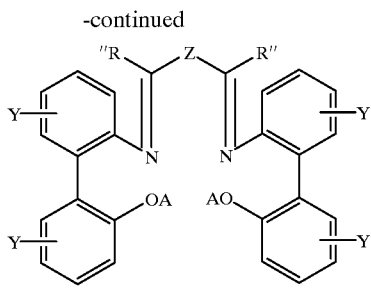

wherein each Y is independently selected from the group consisting of: H, one or more halide, alkyl, aryl, alkoxide, nitro and carboxylate; each R" is independently selected from the group consisting of: H, alkyl, substituted alkyl, aryl, substituted aryl, 1,2-, 1,3- or 1,4-arylene, and a group that is part of an aryl system; Z is selected from the group consisting of: $(CH_2)_n$ wherein n is 0, 1 or 2, $CR_2$ wherein R is alkyl or aryl, aryl, substituted aryl, heteroaryl, phenol and aryl carboxylate; and each A is independently selected from the group consisting of: H, alkyl and substituted alkyl;

wherein D is represented by the formula selected from the group consisting of:

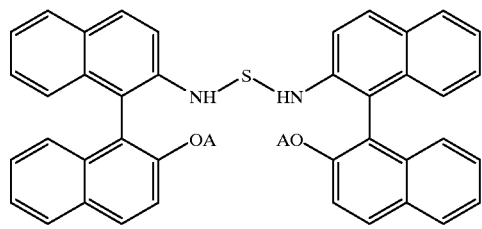

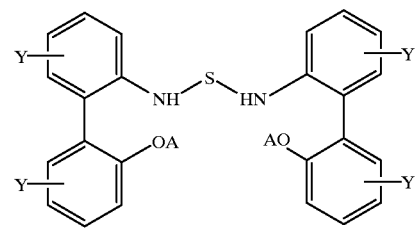

wherein each Y is independently selected from the group consisting of: H, one or more halide, alkyl, aryl, alkoxide, nitro and carboxylate; each R" is independently selected from the group consisting of: H, alkyl, substituted alkyl, aryl, substituted aryl, and a group that is part of an aryl system; S is independently selected from the group consisting of: $(CH_2)_n$ wherein n is 2–6 and $CH_2(Ar)CH_2$ wherein Ar is arylene or substituted arylene; and each A is independently selected from the group consisting of: H, alkyl and substituted alkyl; and wherein E is represented by the formula selected from the group consisting of:

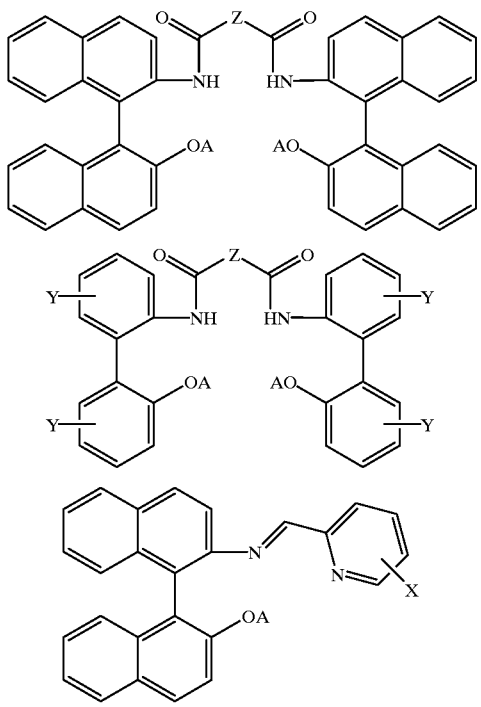

wherein each X and Y is independently selected from the group consisting of: H, one or more halide, alkyl, aryl, alkoxide, nitro and carboxylate; Z is selected from the group consisting of: $(CH_2)_n$ wherein n is 0, 1 or 2, $CR_2$ wherein R is alkyl or aryl, aryl, 1,2-, 1,3- or 1,4-arylene, substituted aryl, heteroaryl, phenol and aryl carboxylate; and each A is independently selected from the group consisting of: H, alkyl and substituted alkyl.

13. The process of claim 12, wherein said asymmetric reaction is selected from the group consisting of: hydrogenation, hydroformylation, allylic alkylation, cyclopropanation, Heck reaction, Aldol reaction, Michael addition and epoxidation.

14. The process of claim 13, wherein said asymmetric reaction is hydrogenation; said substrate is selected from the group consisting of: a ketone, an imine and an alkane; and said catalyst is prepared by contacting a Rh, Ru or Ir salt, or a complex thereof, and a ligand according to any of formulas C, D and E.

15. The process of claim 13, wherein said asymmetric reaction is selected from the group consisting of: allylic alkylation and Heck reaction; said substrate is an ethylenically unsaturated compound; and said catalyst is prepared by contacting a Pd salt, or a complex thereof, and a ligand according to any of formulas C, D and E.

16. The process of claim 13, wherein said asymmetric reaction is hydroformylation; said substrate is an ethylenically unsaturated compound; and said catalyst is prepared by contacting a Rh salt, or a complex thereof, and a ligand according to any of formulas C, D and E.

17. The process of claim 13, wherein said asymmetric reaction is epoxidation; said substrate is an ethylenically unsaturated compound; and said catalyst is prepared by contacting a Ti, V, Mo, Re or Mn salt, or a complex thereof, and a ligand according to any of formulas C, D and E.

18. The process of claim 13, wherein said asymmetric reaction is Michael addition; said substrate is an ethylenically unsaturated compound; and said catalyst is prepared by contacting a Cu or Ni salt, or a complex thereof, and a ligand according to any of formulas C, D and E.

19. The process of claim 13, wherein said asymmetric reaction is cyclopropanation; said substrate is an ethylenically unsaturated compound; and said catalyst is prepared by contacting a Cu salt, or a complex thereof, and a ligand according to formula D.

20. The process of claim 13, wherein said asymmetric reaction is Heck reaction; said substrate is an ethylenically unsaturated compound; and said catalyst is prepared by contacting a Pd salt, or a complex thereof, and a ligand according to formula C, D and E.

21. A ligand selected from the group consisting of:

L15

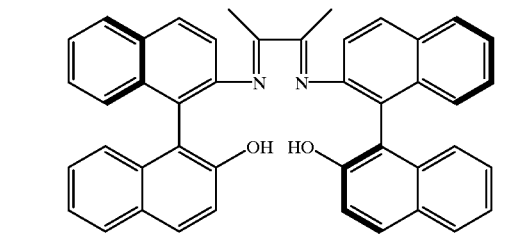

L16

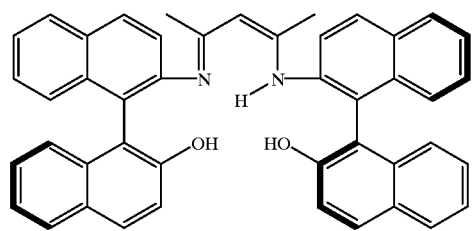

L17

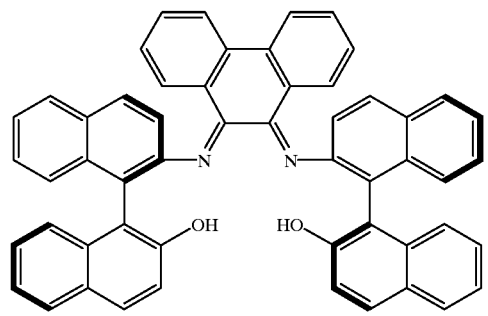

L18

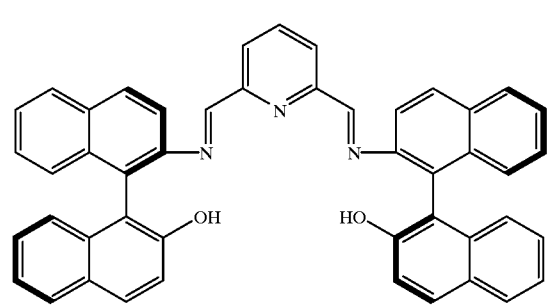

L19

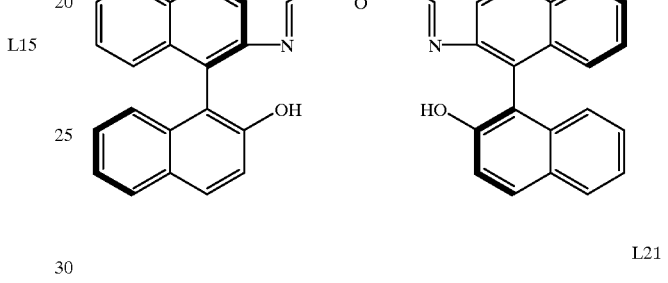

L20

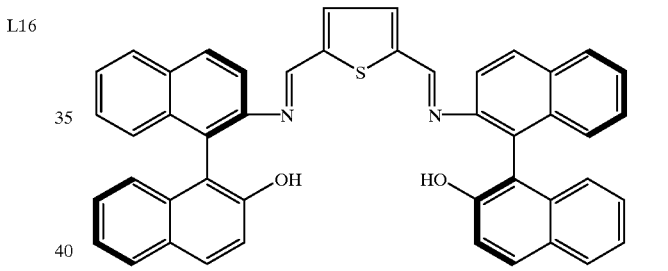

L21

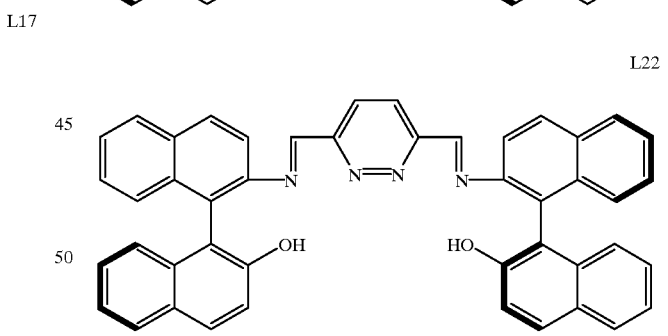

L22

L23

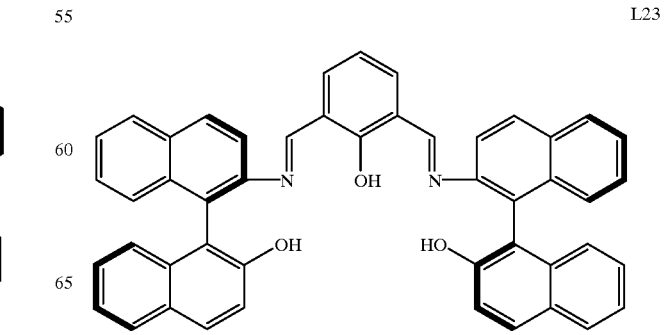

L24
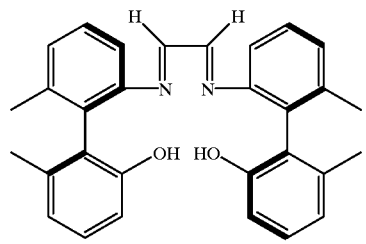
L25
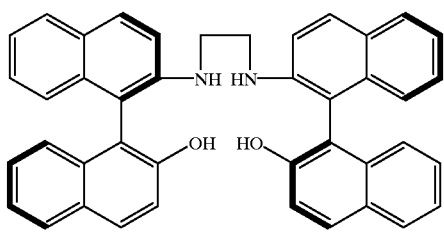
L26
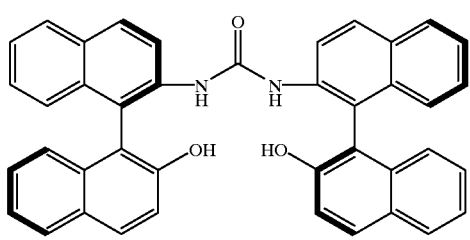
L27
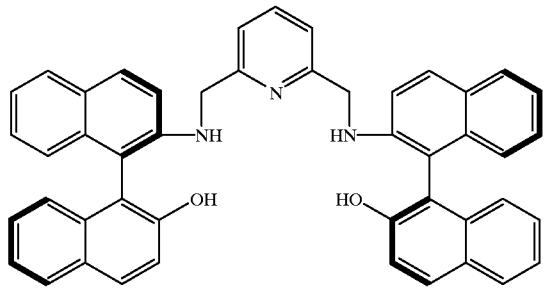
L28
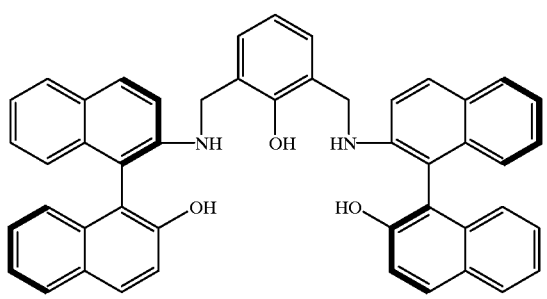
L29
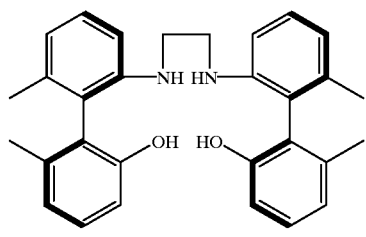
L30
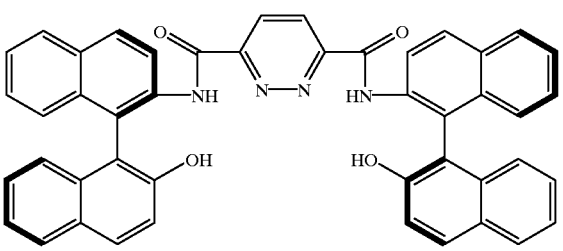
L31
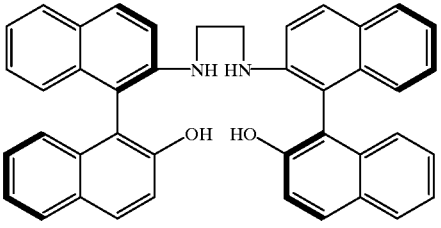
L32
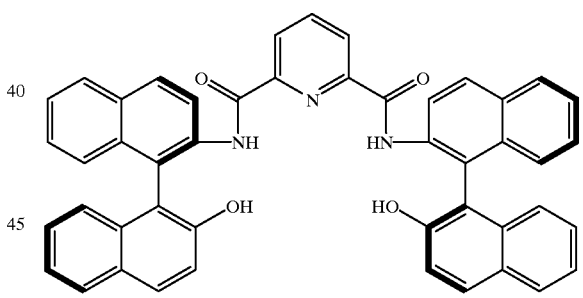
L33
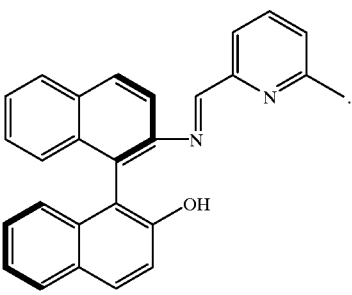
* * * * *

UNITED STATES PATENT AND TRADEMARK OFFICE
CERTIFICATE OF CORRECTION

PATENT NO.   : 6,380,392 B1
DATED        : April 30, 2002
INVENTOR(S)  : Xumu Zhang It is certified that error appears in the above-identified patent and that said Letters Patent is hereby corrected as shown below:

<u>Column 1,</u>
Line 9, please insert the following paragraph:
-- This invention was made with support from the United States Government under Contract No. N00014-96-1-0733. The government has certain rights in the invention. --

Signed and Sealed this

Sixth Day of August, 2002

*Attest:*

*Attesting Officer*

JAMES E. ROGAN
*Director of the United States Patent and Trademark Office*